United States Patent
Eberle et al.

(10) Patent No.: US 6,686,469 B2
(45) Date of Patent: Feb. 3, 2004

(54) PESTICIDAL PYRIMIDINE-DERIVATIVES

(75) Inventors: Martin Eberle, Bottmingen (CH); André Jeanguenat, Basel (CH); Werner Zambach, Bättwil (CH); Arthur Steiger, Arlesheim (CH); Saleem Farooq, Arisdorf (CH)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 10/011,012

(22) Filed: Nov. 5, 2001

(65) Prior Publication Data

US 2003/0004347 A1 Jan. 2, 2003

Related U.S. Application Data

(63) Continuation of application No. PCT/EP00/03920, filed on May 2, 2000.

(30) Foreign Application Priority Data

May 4, 1999 (CH) ................................................ 833/99

(51) Int. Cl.[7] .......................... C07D 24/12; C07D 128/32
(52) U.S. Cl. ....................... 544/319; 544/334; 544/335; 544/242; 544/326; 544/327
(58) Field of Search ................................. 544/334, 335, 544/242, 319, 326, 327

(56) References Cited

PUBLICATIONS

Horst Meyer, Chemical Abstracts, 92:6488 (1980).*

* cited by examiner

*Primary Examiner*—John M. Ford
(74) *Attorney, Agent, or Firm*—Michael U. Lee; John W. Kung

(57) ABSTRACT

The invention relates to compounds of the general formula

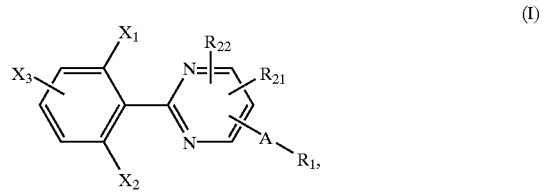

(I)

wherein $R_1$ is unsubstituted or mono- to penta-substituted aryl, whereby the substituents are selected from the group consisting for instance of OH, Halogen, CN, $C_1$–$C_6$-alkyl, optionally substituted $C_3$–$C_8$-cycloalkyl and optionally substituted $C_3$–$C_8$-cycloalkenyl;

A is for instance a single bond, $C_1$–$C_{12}$-alkylene or O;

$X_1$ and $X_2$, independently of one another, are $R_{10}$; $X_3$ is H or $R_{10}$;

$R_{10}$ is for instance halogen, CN, $NO_2$, $C_1$–$C_6$-alkyl, $C_3$–$C_8$-cycloalkyl or $C_1$–$C_6$-haloalkyl;

$R_{21}$ and $R_{22}$, independently of one another are for instance H, halogen, CN, $NO_2$, OH, SH, $C_1$–$C_6$-alkyl, $C_3$–$C_8$-cycloalkyl, $C_1$–$C_6$-alkyl-$C_3$–$C_8$-cycloalkyl or $C_3$–$C_8$-cycloalkyl-$C_1$–$C_6$-alkyl;

$R_{23}$ and $R_{24}$, independently of one another, are for instance H, $C_1$–$C_6$-alkyl, $C_3$–$C_8$-cycloalkyl, $C_3$–$C_8$-cycloalkyl-$C_1$–$C_6$-alkyl, $C_1$–$C_6$-haloalkyl or $C_3$–$C_8$-halocycloalkyl;

m is 1, 2, 3 or 4; and n is 0, 1 or 2;

as well as the physiologically acceptable addition compounds, a method of producing these compounds and the usage of these compounds, pesticide compositions whose active ingredient is chosen from these compounds, each in free form or in agrochemically employable salt form, and a method of producing and using these compositions. The active ingredients, in free form or in agrochemically employable salt form, have advantageous pesticidal properties. The are especially suitable for the control of pests in agriculture and in storage, as well as in the care of domestic animals.

3 Claims, No Drawings

PESTICIDAL PYRIMIDINE-DERIVATIVES

This is a continuation of application No. PCT/EP00/03920 filed May 2, 2000.

The present invention relates to new pyrimidine derivatives of formula

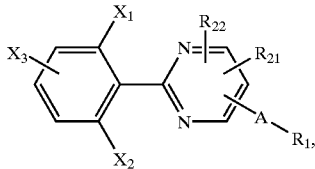

(I)

wherein $R_1$ is unsubstituted or mono- to penta-substituted aryl, whereby the substituents are selected from the group consisting of OH, Halogen, CN, $C_1$–$C_6$-alkyl, optionally substituted $C_3$–$C_8$-cycloalkyl, optionally substituted $C_3$–$C_8$-cycloalkenyl, $C_1$–$C_6$-alkyl-$C_3$–$C_8$-cycloalkyl, $C_3$–$C_8$-cycloalkyl-$C_1$–$C_6$-alkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$-cycloalkylthio, $C_1$–$C_6$-haloalkylthio, $C_3$–$C_8$-halocycloalkylthio, $C_1$–$C_6$-alkylsulfinyl, $C_3$–$C_8$-cycloalkylsulfinyl, $C_1$–$C_6$-haloalkylsulfinyl, $C_3$–$C_8$-halocycloalkylsulfinyl, $C_1$–$C_6$-alkylsulfonyl, $C_3$–$C_8$-cycloalkylsulfonyl, $C_1$–$C_6$-haloalkylsulfonyl, $C_3$–$C_8$-halocycloalkylsulfonyl, optionally substituted $C_2$–$C_8$-alkenyl, optionally substituted $C_2$–$C_8$-alkinyl, $C_1$–$C_6$-alkylcarbonyl, —C(=NOR$_6$)—$C_1$–$C_6$-Alkyl; $R_7$; unsubstituted or mono- to penta-substituted phenyl; unsubstituted or mono- to penta-substituted heteroaryl, whereby the substituents are respectively selected from the group consisting of OH, halogen, CN, NO$_2$, $C_1$–$C_6$-alkyl, $C_3$–$C_8$-cycloalkyl, $C_1$–$C_6$-alkyl-$C_3$–$C_8$-cycloalkyl, $C_3$–$C_8$-cycloalkyl-$C_1$–$C_6$-alkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$cycloalkylthio, $C_1$–$C_6$-haloalkylthio, $C_3$–$C_8$-halocycloalkylthio, $C_3$–$C_8$-alkylsulfinyl, $C_3$–$C_8$cycloalkylsulfinyl, $C_1$–$C_6$-haloalkylsulfinyl, $C_3$–$C_8$-halocycloalkylsulfinyl, $C_1$–$C_6$-alkylsulfonyl, $C_3$–$C_8$-cycloalkylsulfonyl, $C_1$–$C_6$-haloalkylsulfonyl, $C_3$–$C_8$-halocycloalkylsulfonyl, $C_2$–$C_8$-alkenyl, $C_2$–$C_8$-alkinyl, $C_1$–$C_6$-alkylcarbonyl, —C(=NOR$_6$)—$C_1$–$C_6$-Alkyl and $R_7$; unsubstituted or mono- to penta-substituted phenoxy; unsubstituted or mono- to penta-substituted phenylthio; unsubstituted or mono- to penta-substituted phenylamino and unsubstituted or mono- to penta-substituted —N(phenyl)($C_1$–$C_6$-alkyl), whereby the substituents are respectively selected from the group consisting of halogen, CN, NO$_2$, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-alkylthio, $C_3$–$C_8$cycloalkythio, $C_1$–$C_6$-haloalkylthio and $C_3$–$C_8$-halocycloalkylthio;

A is a single bond, $C_1$–$C_{12}$-alkylene, O, O($C_1$–$C_{12}$-alkylene), S(O)$_n$, S(O)$_n$($C_1$–$C_{12}$-alkylene), $C_2$–$C_8$-alkenylene, $C_2$–$C_8$-alkinylene; NR$_3$ or NR$_3$($C_1$–$C_{12}$-alkylene);

$R_3$ is H, $C_1$–$C_6$-alkyl, $C_3$–$C_8$-cycloalkyl, $C_1$–$C_6$-haloalkyl, $C_2$–$C_8$-alkenyl, $C_2$–$C_8$-alkinyl, aryl-$C_1$–$C_6$-alkyl, (CH$_2$)$_p$C(O)R$_4$ or $C_1$–$C_6$-alkoxy-$C_1$–$C_6$-alkyl;

$R_4$ is H, $C_1$–$C_6$-alkyl, $C_3$–$C_8$-cycloalkyl, $C_1$–$C_6$-haloalkyl, $C_1$–$C_6$-alkoxy, N(R$_5$)$_2$ or $C_1$–$C_6$-alkoxy-$C_1$–$C_6$-alkyl;

$R_5$ is H, $C_1$–$C_6$-alkyl, $C_3$–$C_8$-cycloalkyl, $C_1$–$C_6$-haloalkyl, or aryl-$C_1$–$C_6$-alkyl;

$R_6$ is H, $C_1$–$C_6$-alkyl or $C_3$–$C_8$-cycloalkyl;

$R_7$ is

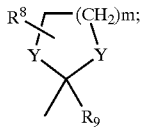

$R_8$ and $R_9$ independently of one another, are H or $C_1$–$C_6$-alkyl;

$X_1$ and $X_2$, independently of one another, are $R_{10}$;

$X_3$ is H or $R_{10}$;

$R_{10}$ is halogen, CN, NO$_2$, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$-cycloalkylthio, $C_1$–$C_6$-haloalkylthio or $C_3$–$C_8$-halocycloalkylthio;

$R_{21}$ and $R_{22}$, independently of one another, are H, halogen, CN, NO$_2$, OH, SH, $C_1$–$C_6$-alkyl, $C_3$–$C_8$-cycloalkyl, $C_1$–$C_6$-alkyl-$C_3$–$C_8$-cycloalkyl, $C_3$–$C_8$-cycloalkyl-$C_1$–$C_6$-alkyl, $C_1$–$C_6$-haloalkyl, halo$C_3$–$C_8$-cycloalkyl, $C_1$–$C_6$-alkoxy, $C_3$–$C_8$-cycloalkoxy, $C_1$–$C_6$-haloalkoxy, halo$C_3$–$C_8$-cycloalkylthio, $C_1$–$C_6$-alkylthio, $C_3$–$C_8$-cycloalkylthio, $C_1$–$C_6$-haloalkylthio, halo$C_3$–$C_8$-cycloalkylthio, $C_1$–$C_6$-alkylsulfinyl, $C_3$–$C_8$-cycloalkylsulfinyl, halo$C_1$–$C_6$-alkylsulfinyl, $C_3$–$C_8$-halocycloalkylsulfinyl, $C_1$–$C_6$-alkylsulfonyl, $C_3$–$C_8$-cycloalkylsulfonyl, $C_1$–$C_6$-haloalkylsulfonyl, halo$C_3$–$C_8$-cycloalkylsufonyl, N(R$_{23}$)R$_{24}$, $C_1$–$C_6$-alkoxy-$C_1$–$C_6$-alkyl, $C_1$–$C_6$-alkoxy-$C_1$–$C_6$-alkoxy, $C_1$–$C_6$-alkoxy-$C_1$–$C_6$-alkylthio, $C_1$–$C_6$-alkoxy-$C_1$–$C_6$-alkylamino, $C_2$–$C_8$-alkenyloxy or $C_2$–$C_8$-alkinyloxy;

$R_{23}$ and $R_{24}$, independently of one another, are H, $C_1$–$C_6$-alkyl, $C_3$–$C_8$-cycloalkyl, $C_3$–$C_8$-cycloalkyl-$C_1$–$C_6$-alkyl, $C_1$–$C_6$-haloalkyl or $C_3$–$C_8$-halocycloalkyl;

m is 1, 2, 3 or 4;

n is 0, 1 or 2; and

Y is O or S;

as well as the physiologically acceptable addition compounds, and where appropriate to E/Z-isomers, to mixtures of E/Z isomers and/or to tautomers, in each case in the free form or in agrochemically employable salt form; a method of producing these compounds and the usage of these compounds, pesticide compositions whose active ingredient is chosen from these compounds, and a method of producing and using these compositions.

Preferred is a compound of the formula (I), wherein $R_1$ is unsubstituted or mono- to penta-substituted aryl, wherein the substituents are selected from the group consisting of OH, Halogen, CN, $C_1$–$C_6$-Alkyl, $C_3$–$C_8$-Cycloalkyl, $C_1$–$C_6$-Alkyl-$C_3$–$C_8$-cycloalkyl, $C_3$–$C_8$-Cycloalkyl-$C_1$–$C_6$-alkyl, $C_1$–$C_6$-Haloalkyl, $C_3$–$C_8$-Halocycloalkyl, $C_1$–$C_6$-Alkoxy, $C_3$–$C_8$-Cycloalkoxy, $C_1$–$C_6$-Haloalkoxy, $C_3$–$C_8$-Halocycloalkoxy, $C_1$–$C_8$-Alkylthio, $C_3$–$C_8$-Cycloalkylthio, $C_1$–$C_6$-Haloalkylthio, $C_3$–$C_8$-Halocycloalkylthio, $C_1$–$C_6$-Alkylsulfinyl, $C_3$–$C_8$-Cycloalkylsulfinyl, $C_1$–$C_6$-Haloalkylsulfinyl, $C_3$–$C_8$-Halocycloalkylsulfinyl, $C_1$–$C_6$-Alkylsulfonyl, $C_3$–$C_8$-Cycloalkylsulfonyl, $C_1$–$C_6$-Haloalkylsulfonyl, $C_3$–$C_8$-Halocycloalkylsulfonyl, $C_2$–$C_8$-Alkenyl, $C_2$–$C_8$-Alkinyl, $C_1$–$C_6$-Alkylcarbonyl, —C(=NOR$_6$)—$C_1$–$C_6$-Alkyl, $R_7$; unsubstituted or mono- to penta-substituted phenyl, wherein the substituents are selected from the group consisting of OH, Halogen, CN, NO$_2$, $C_1$–$C_6$-Alkyl, $C_3-C_8$-Cycloalkyl, $C_1-C_6$-Alkyl-$C_3-C_8$-cycloalkyl, $C_3-C_8$-Cycloalkyl-$C_1-C_6$-alkyl, $C_1-C_6$-Haloalkyl, $C_3-C_8$-Halocycloalkyl, $C_1-C_6$-Alkoxy, $C_3-C_8$-Cycloalkoxy, $C_1-C_6$-Haloalkoxy, $C_3-C_8$-Halocycloalkoxy, $C_1-C_6$-Alkylthio, $C_3-C_8$-Cycloalkylthio, $C_1-C_6$-Haloalkylthio, $C_3-C_8$-Halocycloalkylthio, $C_1-C_6$-Alkylsulfinyl, $C_3-C_8$-Cycloalkylsulfinyl, $C_1-C_6$-Haloalkylsulfinyl, $C_3-C_8$-Halocycloalkylsulfinyl, $C_1-C_6$-Alkylsulfonyl, $C_3-C_8$-Cycloalkylsulfonyl, $C_1-C_6$-Haloalkylsulfonyl, $C_3-C_8$-Halocycloalkylsulfonyl, $C_2-C_8$-Alkenyl, $C_2-C_8$-Alkinyl, $C_1-C_6$-Alkylcarbonyl, —C(=$NOR_6$)—$C_1-C_6$-Alkyl and $R_7$; unsubstituted or mono- to penta-substituted phenoxy, unsubstituted or mono- to penta-substituted phenylthio, unsubstituted or mono- to penta-substituted phenylamino and unsubstituted or mono- to penta-substituted —N(phenyl)($C_1-C_6$-alkyl), wherein the substituents are selected from the group consisting of Halogen, CN, $NO_2$, $C_1-C_6$-Alkyl, $C_3-C_8$-Cycloalkyl, $C_1-C_6$-Haloalkyl, $C_3-C_8$-Halocycloalkyl, $C_1-C_6$-Alkoxy, $C_3-C_8$-Cycloalkoxy, $C_1-C_6$-Alkylthio, $C_3-C_8$-Cycloalkylthio, $C_1-C_6$-Haloalkylthio and $C_3-C_8$-Halocycloalkylthio;

$R_{21}$ and $R_{22}$ independently of one another H, Halogen, CN, $NO_2$, $C_1-C_6$-Alkyl, $C_3-C_8$-Cycloalkyl, $C_1-C_6$-Haloalkyl or $C_3-C_8$-Halocycloalkyl;

A is $(CR_{11}R_{12})_p$, $O(CR_{11}R_{12})_p$, $S(O)_n(CR_{11}R_{12})_p$, unsubstituted or substituted $C_2-C_8$-Alkenylen, unsubstituted or substituted $C_2-C_8$-Alkinylen, wherein the substituents are selected from the group consisting of $R_{11}$ and $R_{12}$; or $NR_3(CH_2)_p$;

$R_3$ is H, $C_1-C_6$-Alkyl, $C_3-C_8$-Cycloalkyl, $C_1-C_6$-Haloalkyl, $C_2-C_8$-Alkenyl, $C_2-C_8$-Alkinyl, Aryl-$C_1-C_6$-alkyl, $(CH_2)_pC(O)R_4$ or $C_1-C_6$-Alkoxy-$C_2-C_6$-alkyl;

$R_4$ is H, $C_1-C_6$-Alkyl, $C_3-C_8$-Cycloalkyl, $C_1-C_6$-Haloalkyl, $C_1-C_6$-Alkoxy, $N(R_5)_2$ or $C_1-C_6$-Alkoxy-$C_2-C_6$-alkyl;

$R_5$ is H, $C_1-C_6$-Alkyl, $C_3-C_8$-Cycloalkyl, $C_1-C_6$-Haloalkyl or Aryl-$C_1-C_6$-alkyl;

$R_6$ is H, $C_1-C_6$-Alkyl or $C_3-C_8$-Cycloalkyl;

$R_7$ is

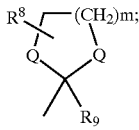

$R_8$ and $R_9$ are independently of one another H or $C_1-C_6$-Alkyl;

$X_1$ and $X_2$ are independently of one another $R_{10}$;

$X_3$ is H or $R_{10}$;

$R_{10}$ is Halogen, CN, $NO_2$, $C_1-C_6$-Alkyl, $C_3-C_8$-Cycloalkyl, $C_1-C_6$-Haloalkyl, $C_3-C_8$-Halocycloalkyl, $C_1-C_6$-Alkoxy, $C_3-C_8$-Cycloalkoxy, $C_1-C_6$-Haloalkoxy, $C_3-C_8$-Halocycloalkoxy, $C_1-C_6$-Alkylthio, $C_3-C_8$-Cycloalkylthio, $C_1-C_6$-Haloalkylthio or $C_3-C_8$-Halocycloalkylthio;

$R_{11}$ and $R_{12}$ independently of one another H or $C_1-C_6$-Alkyl;

m is 1, 2, 3 or 4;

n is 0, 1 or 2;

p is 0, 1, 2, 3, 4, 5 or 6; und

Q is O or S;

and where appropriate to E/Z isomers, to mixtures of E/Z isomers and/or to tautomers, in each case in the free form or in agrochemically employable salt form.

In literature, certain pyrimidine derivatives have been proposed as active ingredients in pesticides for domestic animals and productive livestock, as well as for crops of cultivated plants. The biological properties of these known compounds, however, are not fully satisfactory in the field of pest control, which is why there is a need to provide further compounds with pesticidal properties; this problem is solved according to the invention with the development of the present compounds of formula (I).

The compounds of formula (I) may exist as salts or may form e.g. acid addition salts; the free form however being preferred. The latter are formed for example with strong inorganic acids, typically mineral acids, e.g. sulfuric acid, a phosphoric acid or a hydrohalic acid, or with strong organic carboxylic acids, typically $C_1-C_4$-alkanecarboxylic acids substituted where appropriate for example by halogen, e.g. acetic acid, such as optionally unsaturated dicarboxylic acids, e.g. oxalic, malonic, maleic, fumaric or phthalic acid, typically hydroxycarboxylic acids, e.g. ascorbic, lactic, malic, tartaric or citric acid, or benzoic acid, or with organic sulfonic acids, typically $C_1-C_4$-alkane or arylsulfonic acids substituted where appropriate for example by halogen, e.g. methanesulfonic or p-toluenesulfonic acid. Hereinbefore and hereinafter, the free compounds of formula (I) and their salts are understood where appropriate to include also by analogy the corresponding salts or free compounds of formula (I).

Unless otherwise defined, the general terms used hereinabove and hereinbelow have the meanings given hereinbelow.

Carbon-containing groups and compounds contain, unless otherwise defined, in each case 1 up to and including 6, preferably 1 up to and including 4, in particular 1 or 2, carbon atoms. Aryl is phenyl or naphthyl.

Heteroaryl is especially pyridyl, pyrimidyl, s-triazinyl, 1,2,4-triazinyl, thienyl, furanyl, pyrryl, pyrazolyl, imidazolyl, thiazolyl, triazolyl, oxazolyl, thiadiazolyl, oxadiazolyl, benzothienyl, benzofuranyl, benzothiazolyl, indolyl or indazolyl, which are preferably bonded via a carbon atom; thiazolyl, benzofuranyl, benzothiazolyl or indolyl, especially thiazolyl or indolyl, is preferred.

Halogen—as a group per se or as structural element of other groups and compounds such as haloalkyl, haloalkoxy and haloalkylthio—is fluorine, chlorine, bromine or iodine, in particular fluorine, chlorine or bromine, mainly fluorine or chlorine.

Alkyl—as a group per se and as structural element of other groups and compounds such as haloalkyl, alkoxy, haloalkoxy and alkylthio,—is, in each case with due consideration of the specific number of carbon atoms in the group or compound in question, either straight-chained, i.e. methyl, ethyl, propyl, butyl, pentyl, hexyl, heptyl, or octyl, or branched, for example isopropyl, isobutyl, sec-butyl, tert-butyl, isopentyl, neopentyl or isohexyl.

Cycloalkyl—as a group per se and as structural element of other groups and compounds such as halocycloalkyl, cycloalkoxy and cycloalkylthio,—is, in each case with due consideration of the specific number of carbon atoms in the group or compound in question, cyclopropyl, cyclobutyl, cyclopentyl, cyclohexyl, cycloheptyl or cyclooctyl.

Alkenyl—as a group per se and as structural element of other groups and compounds—is, in each case with due consideration of the specific number of carbon atoms in the group or compound in question and of the conjugated or isolated double bonds—either straight-chained, e.g. allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert.-pentenyl, isohexenyl, isoheptenyl or isooctenyl.

Alkinyl—as a group per se and as structural element of other groups and compounds—is, in each case with due consideration of the specific number of carbon atoms in the group or compound in question and of the conjugated or isolated double bonds—either straight-chained, e.g. propargyl, 2-butinyl, 3-pentinyl, 1-hexinyl, 1-heptinyl, 3-hexen-1-inyl or 1,5-heptadien-3-inyl, or branched, e.g. 3-methylbut-1-inyl, 4-ethylpent-1-inyl, 4-methylhex-2-inyl or 2-methylhept-3-inyl.

Alkylene, alkenylene and alkinylene are straight-chained or branched bridging members; they are, in particular, $-CH_2-$, $-CH_2-CH_2-$, $-CH(CH_3)-$, $-CH(CH_3)CH_2-$, $-CH(CH_3)CH_2-CH_2-$, $-CH_2C(CH_3)_2-CH_2-$, $-CH=CH-$, $-CH_2-CH=CH-$, $-CH_2-CH=CH-CH_2-$; $-C\equiv C-$, and $-CH_2C\equiv C-$; especially $-CH_2-$.

Halogen-substituted carbon-containing groups and compounds, such as haloalkyl, haloalkoxy and haloalkylthio, can be partially halogenated or perhalogenated, in the case of polyhalogenation it being possible for the halogen substituents to be identical or different. Examples of haloalkyl—as a group per se and as structural element of other groups and compounds such as haloalkoxy and haloalkylthio,—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)(CHF)_2CF_3$ or $CH_2(CF_2)_3CF_3$; pentyl or one of its isomers, mono- to undeca-substituted by fluorine, chlorine and/or bromine, such as $CF(CF_3)(CHF)_2CF_3$ or $CH_2(CF_2)_3CF_3$; and hexyl or one of its isomers, mono- to trideca-substituted by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Optionally substituted radicals such as for instance $C_2–C_8$-alkenyl, $C_2–C_8$-alkynyl, $C_3–C_8$-cycloalkenyl or $C_1–C_6$-alkyl, are preferrably substituted with OH, CN, nitro, halogen, $C_1–C_6$-alkoxy, $C_1–C_6$-haloalkoxy, $C_1–C_6$-alkylthio, $C_1–C_6$-haloalkylthio, $C_1–C_6$-alkylsulfinyl, $C_1–C_6$-haloalkylsulfinyl, $C_1–C_6$-alkylsulfonyl, $C_1–C_6$-haloalkylsulfonyl, phenyl, halogenphenyl, phenoxy, $NHR_3$, $-C(=O)NH_2$, $-C(=O)O-C_1–C_6$-alkyl and $-C(=O)-C_1–C_6$-alkyl.

In the context of the invention preferred embodiments are A compound of formula (I), and where appropriate to E/Z isomers, to mixtures of E/Z isomers and/or to tautomers, in each case in the free form or in agrochemically employable salt form, including the physiologically acceptable addition compound, wherein (1) $R_1$ is unsubstituted or mono- to tri-substituted phenyl, whereby the substituents are selected from the group consisting of halogen, CN, $C_1–C_6$-alkyl, $C_3–C_8$-cycloalkyl, $C_1–C_6$-haloalkyl, $C_3–C_8$-halocycloalkyl, $C_1–C_6$-alkoxy, $C_3–C_8$-cycloalkoxy, $C_1–C_6$-haloalkoxy, $C_3–C_8$-halocycloalkoxy, $C_1–C_6$-alkylthio, $C_3–C_8$-cycloalkylthio, $C_1–C_6$-haloalkylthio, $C_3–C_8$-halocycloalkylthio, $C_1–C_6$-alkylsulfinyl, $C_3–C_8$-cycloalkylsulfinyl, $C_1–C_6$-haloalkylsulfinyl, $C_3–C_8$-halocycloalkylsulfinyl, $C_1–C_6$-alkylsulfonyl, $C_3–C_8$-cycloalkylsulfonyl, $C_1–C_6$-haloalkylsulfonyl, $C_3–C_8$-halocycloalkylsulfonyl; unsubstituted or mono- to tri-substituted phenyl, whereby the substituents are selected from the group consisting of halogen, CN, $NO_2$, $C_1–C_6$-alkyl, $C_3–C_8$-cycloalkyl, $C_1–C_6$-haloalkyl, $C_3–C_8$-halocycloalkyl, $C_1–C_6$-alkoxy, $C_3–C_8$-cycloalkoxy, $C_1–C_6$-haloalkoxy, $C_3–C_8$-halocycloalkoxy, $C_1–C_6$-alkylthio, $C_3–C_8$-cycloalkylthio, $C_1–C_6$-haloalkylthio, $C_3–C_8$-halocycloalkylthio, $C_1–C_6$-alkylsulfinyl, $C_3–C_8$-cycloalkylsulfinyl, $C_1–C_6$-haloalkylsulfinyl, $C_3–C_8$-halocycloalkylsulfinyl, $C_1–C_6$-alkylsulfonyl, $C_3–C_8$-cycloalkylsulfonyl, $C_1–C_6$-haloalkylsulfonyl and $C_3–C_8$-halocycloalkylsulfonyl; unsubstituted or mono- to tri-substituted phenoxy, unsubstituted or mono- to tri-substituted phenylthio, unsubstituted or mono- to tri-substituted phenylamino and unsubstituted or mono- to tri-substituted $-N(phenyl)(C_1–C_6\text{-alkyl})$, whereby the substituents are respectively selected from the group consisting of halogen, CN, $NO_2$, $C_1–C_6$-alkyl, $C_3–C_8$-cycloalkyl, $C_1–C_6$-haloalkyl, $C_3–C_8$-halocycloalkyl, $C_1–C_6$-alkoxy, $C_1–C_6$-haloalkoxy, $C_1–C_6$-alkylthio, $C_1–C_6$-haloalkylthio, $C_1–C_6$-alkylsulfinyl, $C_1–C_6$-alkylsulfonyl, $C_1–C_6$-haloalkylsulfinyl, $C_1–C_6$-haloalkylsulfonyl and $C_3–C_8$-cycloalkoxy;

preferably mono- or di-substituted phenyl, whereby the substituents are selected from the group consisting of halogen, CN, $C_1–C_6$-alkyl, $C_3–C_8$-cycloalkyl, $C_1–C_6$-haloalkyl, $C_3–C_8$-halocycloalkyl, $C_1–C_6$-alkoxy, $C_3–C_8$-cycloalkoxy, $C_1–C_6$-haloalkoxy, $C_3–C_8$-halocycloalkoxy, unsubstituted or mono- to tri-substituted phenyl, whereby the substituents are selected from the group consisting of halogen, CN, $NO_2$, $C_1–C_6$-alkyl, $C_3–C_8$-cycloalkyl, $C_1–C_6$-haloalkyl, $C_3–C_8$-halocycloalkyl, $C_1–C_6$-alkoxy, $C_3–C_8$-cycloalkoxy, $C_1–C_6$-haloalkoxy and $C_3–C_8$-halocycloalkoxy; unsubstituted or mono- to tri-substituted phenoxy and unsubstituted or mono- to tri-substituted phenylamino, whereby the substituents of the said phenoxy-phenylamino-radicals are selected from the group consisting of halogen, CN, $NO_2$, $C_1–C_4$-alkyl, $C_3–C_6$-cycloalkyl, $C_1–C_4$-haloalkyl, $C_3–C_6$-halocycloalkyl, $C_1–C_4$-alkoxy, $C_3–C_6$-cycloalkoxy, $C_1–C_4$-alkylthio and $C_1–C_4$-haloalkylthio;

more preferably mono- or di-substituted phenyl, whereby the substituents are selected from the group consisting of halogen, $C_1–C_4$-alkyl, $C_1–C_4$-haloalkyl, $C_1–C_4$-alkoxy, $C_1–C_4$-haloalkoxy, unsubstituted or mono- to tri-substituted phenyl, whereby the substituents are selected from the group consisting of halogen, CN, $NO_2$, $C_1–C_4$-alkyl, $C_1–C_4$-haloalkyl, $C_1–C_4$-alkoxy and $C_1–C_4$-haloalkoxy, unsubstituted or mono- to tri-substituted phenoxy and unsubstituted or mono- to tri-substituted phenylamino, whereby the substituents are selected from the group consisting of halogen, $C_1–C_4$-alkyl, $C_1–C_4$-haloalkyl, $C_1–C_6$-alkoxy, $C_1–C_6$-haloalkoxy, $C_1–C_6$-alkylthio and $C_1–C_6$-haloalkylthio;

most preferably monosubstituted phenyl, whereby the substituents are selected from the group consisting of fluorine, chlorine, $C_1–C_2$-alkyl, $C_1–C_2$-haloalkyl, and unsubstituted or mono- or di-substituted phenyl, whereby the substituents are selected from the group consisting of fluorine, chlorine, $C_1–C_2$-haloalkyl, $C_1–C_2$-alkoxy, $C_1–C_2$-haloalkoxy, $C_1–C_2$-alkylthio and $C_1–C_2$-haloalkylthio;

very especially monosubstituted phenyl, whereby the substituent is mono- or di-substituted phenyl, whereby the substituents are selected from the group consisting of fluorine, chlorine, $C_1–C_2$-haloalkyl, $C_1–C_2$-alkoxy, $C_1$–$C_2$-haloalkoxy, $C_1$–$C_2$-alkylthio and $C_1$–$C_2$-haloalkylthio;

(2) $R_{21}$ and $R_{22}$, independently of one another, are H, halogen, $C_1$–$C_4$-alkyl or $C_1$–$C_6$-haloalkyl;
   preferably H or halogen;
   most preferably H;

(3) A is a single bond, $C_1$–$C_6$-alkylene, O,O($C_1$–$C_6$-alkylene), $C_2$–$C_4$-alkenylene, $C_2$–$C_4$-alkinylene or $NR_3$;
   preferably a single bond, O, O—$CH_2$—, C≡C, CH═CH or NH;
   more preferably a single bond or O;
   most preferably a single bond;

(4) $R_3$ is H, $C_1$–$C_6$-alkyl or $C_1$–$C_6$-haloalkyl;
   preferably H or $C_1$–$C_6$-alkyl;
   most preferably H or $C_1$–$C_2$-alkyl;

(5) $X_1$ and $X_2$, independently of one another, are halogen, $C_1$–$C_4$-alkyl, $C_3$–$C_6$-cycloalkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;
   preferably halogen, $C_1$–$C_2$-alkyl, $C_1$–$C_2$-haloalkyl, $C_1$–$C_2$-alkoxy or $C_1$–$C_2$-haloalkoxy;
   especially fluorine, chlorine, methyl, trifluoromethyl or methoxy;
   particularly chlorine or fluorine; most particularly fluorine;

(6) $X_3$ is H, halogen, $C_1$–$C_4$-alkyl, $C_3$–$C_6$-cycloalkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;
   preferably H, halogen, $C_1$–$C_2$-alkyl, $C_1$–$C_2$-haloalkyl, $C_1$–$C_2$-alkoxy or $C_1$–$C_2$-haloalkoxy; most preferably H, fluorine, chlorine, methyl, trifluoromethyl or methoxy,
   particularly H, fluorine or chlorine; most particularly H;

(7) $R_1$ is unsubstituted or mono- to tri-substituted phenyl, whereby the substituents are selected from the group consisting of halogen, CN, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$-cycloalkylthio, $C_1$–$C_6$-haloalkylthio, $C_3$–$C_8$-halocycloalkylthio, $C_1$–$C_6$-alkylsulfinyl, $C_3$–$C_8$-cycloalkylsulfinyl, $C_1$–$C_6$-haloalkylsulfinyl, $C_3$–$C_8$-halocycloalkylsulfinyl, $C_1$–$C_6$-alkylsulfonyl, $C_3$–$C_8$-cycloalkylsulfonyl, $C_1$–$C_6$-haloalkylsulfonyl, $C_3$–$C_8$-halocycloalkylsulfonyl; unsubstituted or mono- to tri-substituted phenyl, whereby the substituents are selected from the group consisting of halogen, CN, $NO_2$, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$-cycloalkylthio, $C_1$–$C_6$-haloalkylthio, $C_3$–$C_8$-halocycloalkylthio, $C_1$–$C_6$-alkylsulfinyl, $C_3$–$C_8$-cycloalkylsulfinyl, $C_1$–$C_6$-haloalkylsulfinyl, $C_3$–$C_8$-halocycloalkylsulfinyl, $C_1$–$C_6$-alkylsulfonyl, $C_3$–$C_8$-cycloalkylsulfonyl, $C_1$–$C_6$-haloalkylsulfonyl and $C_3$–$C_8$-halocycloalkylsulfonyl; unsubstituted or mono- to tri-substituted phenoxy, unsubstituted or mono- to tri-substituted phenylthio, unsubstituted or mono- to tri-substituted phenylamino and unsubstituted or mono- to tri-substituted —N(phenyl)($C_1$–$C_6$-alkyl), whereby the substituents of the phenoxy-, phenylthio-, phenylamino- and —N(phenyl)($C_1$–$C_6$-alkyl)radicals respectively are selected from the group consisting of halogen, CN, $NO_2$, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$haloalkylsulfinyl, $C_1$–$C_6$-alkylsulfonyl, $C_1$–$C_6$-haloalkylsulfonyl, and $C_3$–$C_8$-cycloalkoxy;

$R_{21}$ and $R_{22}$, independently of one another, are H, halogen, $C_1$–$C_4$-alkyl or $C_1$–$C_6$-haloalkyl;

A is a single bond, $C_1$–$C_{12}$-alkylene, O, O($C_1$–$C_{12}$-alkylene), $C_2$–$C_8$-alkenylene, $C_2$–$C_8$-alkinylene; or $NR_3$;

$R_3$ is H, $C_1$–$C_6$-alkyl or $C_1$–$C_6$-haloalkyl;

$X_1$ and $X_2$, independently of one another, are halogen, $C_1$–$C_4$-alkyl, $C_3$–$C_6$-cycloalkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; and $X_3$ is H, halogen, $C_1$–$C_4$-alkyl, $C_3$–$C_6$-cycloalkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

(8) $R_1$ is mono- or di-substituted phenyl, whereby the substituents are selected from the group consisting of halogen, CN, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, unsubstituted or mono- to tri-substituted phenyl, whereby the substituents are selected from the group consisting of halogen, CN, $NO_2$, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy and $C_3$–$C_8$-halocycloalkoxy, unsubstituted or mono- to tri-substituted phenoxy and unsubstituted or mono- to tri-substituted phenylamino, whereby the substituents are selected from the group consisting of halogen, CN, $NO_2$, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_1$–$C_6$-haloalkoxy and $C_3$–$C_8$-cycloalkoxy;

$R_{21}$ and $R_{22}$, independently of one another, are H or halogen;

A is a single bond, O, C≡C, CH═CH or NH;

$X_1$ and $X_2$, independently of one another, are halogen, $C_1$–$C_2$-alkyl, $C_1$–$C_2$-haloalkyl, $C_1$–$C_2$-alkoxy or $C_1$–$C_2$-haloalkoxy; and $X_3$ is H, halogen, $C_1$–$C_2$-alkyl, $C_1$–$C_2$-haloalkyl, $C_1$–$C_2$-alkoxy or $C_1$–$C_2$-haloalkoxy;

(9) $R_1$ is mono- or di-substituted phenyl, whereby the substituents are selected from the group consisting of halogen, $C_1$–$C_4$-alkyl, $C_1$–$C_4$-haloalkyl, $C_1$–$C_4$-alkoxy, $C_1$–$C_4$-haloalkoxy; unsubstituted or mono- to tri-substituted phenyl, whereby the substituents are selected from the group consisting of halogen, CN, $NO_2$, $C_1$–$C_4$-alkyl, $C_1$–$C_4$-haloalkyl, $C_1$–$C_4$-alkoxy, $C_1$–$C_4$-haloalkoxy, $C_1$–$C_6$-alkylthio and $C_1$–$C_6$-haloalkylthio; and unsubstituted or mono- to tri-substituted phenoxy, whereby the substituents are selected from the group consisting of halogen, $C_1$–$C_4$-alkyl, $C_1$–$C_4$-haloalkyl and $C_1$–$C_6$-alkoxy;

$R_{21}$ and $R_{22}$ are H;

A is a single bond;

$X_1$ and $X_2$, independently of one another, are halogen, $C_1$–$C_2$-alkyl, $C_1$–$C_2$-haloalkyl, $C_1$–$C_2$-alkoxy or $C_1$–$C_2$-haloalkoxy; and $X_3$ is H, halogen, $C_1$–$C_2$-alkyl, $C_1$–$C_2$-haloalkyl, $C_1$–$C_2$-alkoxy or $C_1$–$C_2$-haloalkoxy;

(10) $R_1$ is mono- or di-substituted phenyl, whereby the substituents are selected from the group consisting of halogen, $C_1$–$C_2$-alkyl, $C_1$–$C_2$-haloalkyl; and unsubstituted or mono- or di-substituted phenyl, whereby the substituents are selected from the group consisting of halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;

$R_{21}$ and $R_{22}$ are H;

A is a single bond;

$X_1$ and $X_2$, independently of one another, are fluorine, chlorine, methyl, trifluoromethyl or methoxy; and $X_3$ is H, fluorine, chlorine, methyl, trifluoromethyl or methoxy;

(11) the group A—$R_1$ is in the 5-position of the pyrimidine ring.

The compounds of formula (I) which are especially preferred in the context of the invention are those listed in Tables 1 to 4, and those most particularly preferred are those named in the synthesis examples.

A further object of the invention is a method of preparing the compounds of formula (I), in each case in free form or in the form of a salt, wherein a) in order to produce a compound of formula (I), wherein $R_2$, and $R_{22}$ are other than halogen and $AR_1$ is in 5-position, a compound of formula

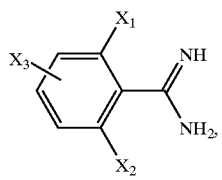 (II)

which is known or may be produced analogously to corresponding known compounds, and wherein $X_1$, $X_2$ and $X_3$ are defined as given for formula (I), in free form or in salt form, is reacted with a compound of formula

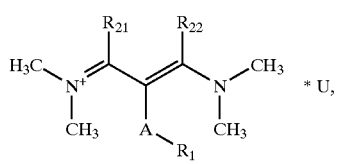 (III)

wherein U is a anion such as a halogenide, sulfate, perchlorate or nitrate, and which is known or may be produced analogously to corresponding known compounds, and wherein A, $R_1$, $R_2$, and $R_{22}$ are defined as given for formula (I), optionally in the presence of a base catalyst such as sodium methylate, or b) in order to produce a compound of formula (I), wherein A is alkylene, $C_2$–$C_8$-alkenylene or $C_2$–$C_8$-alkinylene and $R_{22}$ is other than halogen, a compound of formula (II), in free form or in salt form, is reacted with a compound of formula

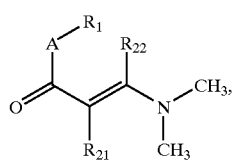 (IV)

which is known or may be produced analogously to corresponding known compounds, and wherein $R_1$, $R_{21}$, and $R_{22}$ are defined as given for formula (I), and A is alkylene, $C_2$–$C_8$-alkenylene or $C_2$–$C_8$-alkinylene, optionally in the presence of a base catalyst such as sodium methylate, or b) in order to produce a compound of formula (I), wherein A is O, $O(C_1$–$C_{12}$-alkylene) $S(O)_n$ or $S(O)_n(C_1$–$C_{12}$-alkylene) and $R_{22}$ is other than halogen, a compound of formula (II), in free form or in salt form, is reacted with a compound of formula

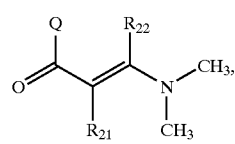 (V)

which is known or may be produced analogously to corresponding known compounds, and wherein $R_{21}$ and $R_{22}$ are defined as for formula (I) and Q is a leaving group, preferably a halogen or $C_1$–$C_6$-alkoxy radical, and the resulting product, optionally after intermediate isolation, is reacted with a halogenation agent, preferably $PCl_5$, $POCl_3$ or $(COCl)_2$, and the resulting product, optionally after renewed intermediate isolation, is reacted with a compound of formula

 HA—$R_1$ (VI), which is known or may be produced analogously to corresponding known compounds, and wherein A and $R_1$ are defined as given for formula (I), optionally in the presence of a base catalyst, or d) in order to produce a compound of formula

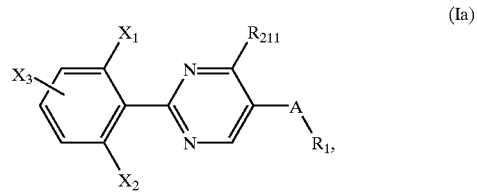 (Ia)

wherein $X_1$, $X_2$, $X_3$, A and $R_1$ are defined as above for formula (I), and $R_{211}$ is halogen, OH, SH, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$-cycloalkylthio, $C_1$–$C_6$-haloalkylthio, $C_3$–$C_8$-halocycloalkylthio, $C_1$–$C_6$-alkylsulfinyl, $C_3$–$C_8$-cycloalkylsulfinyl, $C_1$–$C_6$-haloalkylsulfinyl, $C_3$–$C_8$-halocycloalkylsulfinyl, $C_1$–$C_6$-alkylsulfonyl, $C_3$–$C_8$-cycloalkylsulfonyl, $C_1$–$C_6$-haloalkylsulfonyl, $C_3$–$C_8$-halocycloalkylsulfonyl, $N(R_{23})R_{24}$, $C_1$–$C_6$-alkoxy-$C_1$–$C_6$-alkoxy, $C_1$–$C_6$-alkoxy-$C_1$–$C_6$-alkylthio, $C_1$–$C_6$-alkoxy-$C_1$–$C_6$-alkylamino, $C_2$–$C_8$-alkenyloxy or $C_2$–$C_8$-alkinyloxy and $R_{23}$ and $R_{24}$ are defined as above for formula (I), a compound of the above formula (II) is reacted with a compound of formula

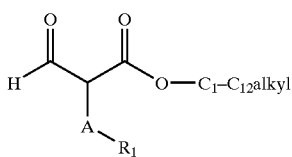

(VII)

wherein A and $R_1$ are defined as above for formula (I), and the compound of formula (Ia) thus obtained, wherein $R_{211}$ is OH, is optionally reacted with a halogenation agent to form a compound of formula (Ia) wherein $R_{211}$ is halogen, especially chlorine, and the compound of formula (Ia) thus obtained, wherein $R_{211}$ is halogen, is optionally reacted with a compound of formula

(VII), wherein Z is O or S and $R_x$ is H, $C_1$–$C_6$-alkyl, $C_3$–$C_8$-cycloalkyl, $C_1$–$C_6$-haloalkyl, halo-$C_3$–$C_8$-cycloalkyl, $C_1$–$C_6$-alkoxy-$C_1$–$C_6$-alkyl, $C_2$–$C_8$-alkenyl or $C_2$–$C_8$-alkinyl;
or with a compound of formula

(IX), wherein $R_{23}$ and $R_{24}$ have the significances given in formula (I),
and the compounds of formula (Ia) thus obtained, wherein the substituent $R_{211}$ is bonded by a S-atom to the pyrimidine ring, is optionally oxidised, or e) in order to produce a compound of formula

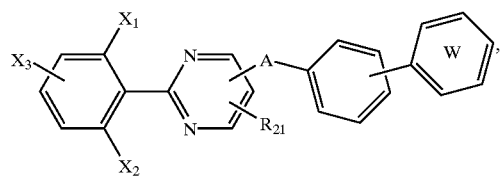

(Ib)

wherein A, $X_1$, $X_2$, $X_3$ $R_{21}$ are defined as above for formula (I) and the ring marked W is substituted as indicated in formula (I), a compound of formula

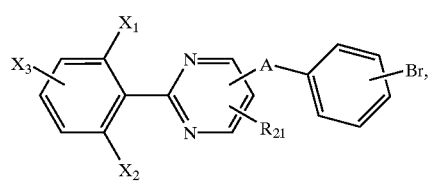

(Ic)

wherein $X_1$, $X_2$, $X_3$ $R_{21}$ are defined as above for formula (I), is reacted with a compound of formula

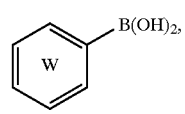

(X)

which is optionally substituted in the ring marked W as indicated in formula (Ic), and which is known or may be produced by methods known per se;

and in each case, if so desired, a compound of formula (I) obtainable according to the method or by other means, present in free form or in the form of a salt, is converted into a different compound of formula (I), a mixture of isomers obtainable according to the method is separated and the desired isomer is isolated and/or a free compound of formula (I) obtainable according to the method is converted into a salt, or a salt obtainable according to the method from a compound of formula (I) is converted into the free compound of formula (I) or into a different salt.

The statement made hereinabove with regard to salts of formula (I) applies by analogy in respect of the salts of starting materials mentioned hereinbefore and hereinafter.

The reaction partners in the reactions steps a to h) can be reacted with one another as they are, i.e. without the addition of a solvent or diluent, e.g. in the melt. In most cases, however, the addition of an inert solvent or diluent, or a mixture thereof, is of advantage.

Variant a):

Examples of solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxan; ketones such as acetone, methyl ethyl ketone or methyl isobutyl ketone; alcohols such as methanol, ethanol, propanol, isopropanol, butanol, ethylene glycol or glycerol; and sulfoxides, such as dimethyl sulfoxide. If the reaction takes place in the presence of a base, then bases used in excess, such as triethylamine, pyridine, N-methylmorpholine, or N,N-diethylaniline, can also serve as solvents or diluents. Alcohols are preferred.

The reaction is advantageously carried out within a temperature range of about 0° C. to about +150° C., preferably 20° C. to about +100° C.

In a preferred embodiment of variant a), a compound of formula (II) in salt form is reacted at ca. 50° to 100°, preferably ca. 65°, in an alcohol, preferably methanol, in the presence of a basic catalyst, preferably sodium methanolate, with a compound of formula (III)

Variant b):

Examples of solvents or diluents are named under variant a).

The reaction is advantageously carried out within a temperature range of about 0° C. to about +150° C., preferably 20° C. to about +100° C.

In a preferred embodiment of variant b), a compound of formula (II) is reacted at ca. 50° to 100°, preferably ca. 80°, in an alcohol, preferably ethanol, in the presence of a basic catalyst, preferably potassium t.-butylate, with a compound of formula (IV).

Variant c):

Examples of solvents or diluents are named under variant a).

The reaction is advantageously carried out within a temperature range of about 0° C. to about +150° C., preferably 20° C. to about +100° C.

In a preferred embodiment of variant c), a compound of formula (II) is reacted at ca. 50° to 100°, preferably ca. 80°, in an alcohol, preferably ethanol, in the presence of a basic catalyst, preferably potassium t.-butylate, with a compound of formula (V), the resulting intermediate is isolated, reacted in an inert solvent, preferably a polychlorinated aromatic, with POCl$_3$, and the resulting product is reacted, after further isolation, with a compound of formula (VI).

Variant d):

Examples of solvents or diluents are named under variant a).

The reaction is advantageously carried out within a temperature range of about 0° C. to about +150° C., preferably 20° C. to about +100° C.

In a preferred embodiment, a compound of the formula (II) is reacted with a compound of the formula (VII) at 50 to 150° C., preferrably at about 120° C., in toluene, in the presence of an organic base such as triethylamine, or in the presence of an acid such as toluenesulfonic acid. The thus obtained intermediate is reacted with a chlorinating agent such as POCl$_3$, and further reacted with a compound of the formula (VII) or of the formula (IX).

Variant e):

Examples of solvents or diluents are named under variant a).

The reaction is advantageously carried out within a temperature range of about 0° C. to about +150° C., preferably 20° C. to about +100° C.

In a preferred embodiment the compound of the formula (Ic) is reacted with a compound of the formula (X) at about 40 to 90° C., preferrably at about 60° C., in dimethoxyethane, in the presence of a Pd-complex catalyst, for instance Pd(PPh$_3$)$_2$Cl$_2$, and in the presence of aqueous NaHCO$_3$.

A further object of the invention is f) a method of producing the compounds of formula (II), wherein a compound of formula

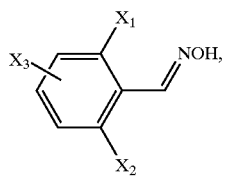

(XII)

which is known or may be produced analogously to corresponding known compounds, and wherein X$_1$, X$_2$ and X$_3$ are defined as for formula (I), is treated with an alkyl hypochlorite, preferably, chlorine, t.-butyl hypochlorite or N-chlorosuccinimide, the resulting intermediate is reacted with ammonia without isolation, and the resulting hydroxamic acid amide is hydrogenated, optionally after intermediate isolation, in the presence of a hydrogenation catalyst, preferably nickel;

and in each case, if so desired, a compound of formula (II) obtainable according to the method or by other means, present in free form or in the form of a salt, is converted into a different compound of formula (II), a mixture of isomers obtainable according to the method is separated and the desired isomer is isolated and/or a free compound of formula (II) obtainable according to the method is converted into a salt, or a salt obtainable according to the method from a compound of formula (II) is converted into the free compound of formula (II) or into a different salt.

Examples of solvents or diluents of step variant f) are named in variant a) for the production of a compound of formula (I).

The reaction is advantageously carried out within a temperature range of about −20° C. to about +100° C., preferably 0° C. to about +30° C.

In a preferred embodiment, a compound of formula (XII) is treated in an inert solvent, preferably methylene chloride, at room temperature with t.-butylhypochlorite, the product is further reacted without isolation with an alcoholic ammonia solution, and after isolation of the intermediate is hydrogenated using nickel as the catalyst.

A further object of the invention is g) a method of producing the compounds of formula (III), e.g. whereby a compound of formula

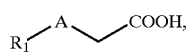

which is known or may be produced analogously to corresponding known compounds, and wherein A and R$_1$ are defined as given for formula (I), is reacted with a mixture of dimethylformamide and POCl$_3$ and in each case, if so desired, a compound of formula (III) obtainable according to the method or by other means, present in free form or in the form of a salt, is converted into a different compound of formula (III), a mixture of isomers obtainable according to the method is separated and the desired isomer is isolated and/or a free compound of formula (III) obtainable according to the method is converted into a salt, or a salt obtainable according to the method from a compound of formula (III) is converted into the free compound of formula (III) or into a different salt.

Examples of solvents or diluents of step variant g) are named in variant a) for the production of a compound of formula (I).

The reaction is advantageously carried out within a temperature range of about −20° C. to about +100° C., preferably −10° C. to about +80° C.

In a preferred embodiment, a compound of formula (XII) is reacted at ca. 20° to 80° without a solvent with a mixture of dimethylformamide and POCl$_3$.

A further object of the invention is h) a method of producing the compounds of formula (IV), whereby a compound of formula

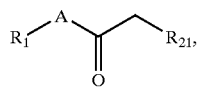

(XIII)

which is known or may be produced analogously to corresponding known compounds, and wherein A and R$_1$ are defined as given for formula (I), except that A is other than O, O(C$_1$–C$_{12}$-alkylene), S(O)$_n$, S(O)$_n$(C$_1$–C$_{12}$-alkylene), NR$_3$ or NR$_3$(C$_1$–C$_{12}$-alkylene), is reacted with a compound of formula

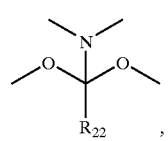

(XIV)

which is known or may be produced analogously to corresponding known compounds, and wherein R$_{22}$ is defined as given for formula (I)

and in each case, if so desired, a compound of formula (IV) obtainable according to the method or by other means, present in free form or in the form of a salt, is converted into a different compound of formula (IV), a mixture of isomers obtainable according to the method is separated and the desired isomer is isolated and/or a free compound of formula (IV) obtainable according to the method is converted into a salt, or a salt obtainable according to the method from a compound of formula (IV) is converted into the free compound of formula (IV) or into a different salt.

Examples of solvents or diluents of step variant h) are named in variant a) for the production of a compound of formula (I).

The reaction is advantageously carried out within a temperature range of about −20° C. to about +100° C., preferably −10° C. to about +80° C.

In a preferred embodiment, a compound of formula (XIII) is reacted at ca. 20° to 80° without a solvent with a mixture of dimethylformamide and $POCl_3$.

Salts of compounds of formula (I) may be prepared in a known manner. Acid addition salts, for example, are obtainable from compounds of formula (I) by treating with a suitable acid or a suitable ion exchange reagent, and salts with bases are obtainable by treating with a suitable base or a suitable ion exchange reagent.

Salts of compounds of formula (I) can be converted into the free compounds of formula (I) by the usual means, acid addition salts e.g. by treating with a suitable basic composition or with a suitable ion exchange reagent, and salts with bases e.g. by treating with a suitable acid or a suitable ion exchange reagent.

Salts of compounds of formula (I) can be converted into other salts of compounds of formula (I) in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds of formula (I) with salt-forming characteristics can be obtained in free form or in the form of salts.

The compounds of formula (I) may be obtained in the form of their solvates, for example hydrates.

The invention relates to all those embodiments of the method, according to which one starts from a compound obtainable as a primary material or an intermediate at any stage of the method and carries out all or some of the missing steps, or uses, or—especially under the reaction conditions—produces a starting material in the form of a derivative or a salt.

In the method of the present invention, the starting materials and intermediates used are preferably those that lead to the compounds of formula (I) described at the beginning as being especially useful.

The invention relates in particular to the methods described in the preparation examples.

Starting materials and intermediates, respectively in free form or in salt form, which are used according to the invention to produce the compounds of formula (I) or salts thereof, and which are new, as well as their use and methods of producing them, similarly form an object of the invention.

The compounds of formula (I) according to the invention are active substances of preventive and/or curative merit for use in pest control and offer a very favourable spectrum of biocidal activity with favourable tolerability in warm-blooded animals, fish, and plants even at low concentrations. The active ingredients according to the invention are active against all or individual development stages of animal pests showing normal sensitivity, as well as those showing resistance, such as insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

The said animal pests include, for example, those which are mentioned in the European Patent application EP-A-736'252 . The pests mentioned therein are thus included by reference in the object of the present invention.

The members of the order Acarina in question are, in particular

*Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcoptes spp., Tarsonemus spp. and Tetranychus spp.

Pests of said type which occur on plants, especially on crops and ornamentals in agriculture, horticulture and forestry, or on parts of such plants, such as fruits, blooms, leaves, stems, tubers or roots, can be controlled, i.e. kept in check or eradicated, using the active ingredients of the invention, this protection remaining for parts of some plants whose growth does not occur until later.

The target crops in question include both natural and modified crops, the crops being modified by breeding or genetically, especially cereals, such as wheat, barley, rye, oats, rice, corn or sorghum; beet, such as sugar beet or fodder beet; fruit, e.g. pomes, drupes and soft fruit, such as apples, pears, plums, peaches, almonds, cherries or berries, e.g. strawberries, raspberries or blackberries; leguminous plants, such as beans, lentils, peas or soybean; oleaginous fruits, such as rape, mustard, poppy, olives, sunflowers, coconut, castor oil plants, cocoa beans or groundnuts; cucumber plants, such as squashes, cucumbers or melons; fibrous plants, such as cotton, flax, hemp or jute; citrus fruits, such as oranges, lemons, grapefruit or mandarins; vegetables, such as spinach, lettuce, asparagus, cabbages, carrots, onions, tomatoes, potatoes or paprika; lauraceae, such as avocado, cinnamon or camphor; and tobacco, nuts, coffee, aubergines, sugar cane, tea, pepper, vines, hops, banana plants, natural rubber plants and ornamentals.

The active ingredients according to the invention are especially suitable for the control of insects and members of the order Acarina, especially phytotoxic eating insects such as *Anthonomus grandis, Diabrotica balteata, Heliothis virescens* larvae, *Plutella xylostella* and *Spodoptera littoralis* larvae, and spider mites, such as Tetranychus spp., in crops of cotton, fruit, citrus, corn, soybean, rape and vegetables.

Other indication areas for the active ingredients of the invention are the protection against pests of the type mentioned of stored products and stores and of material and, in the hygiene sector, in particular the protection of warm-blooded animals, including farm animals, such as cows, pigs, sheep and goats, poultry such as chickens, turkeys and geese, fur-bearing animals such as mink, foxes, chinchillas, rabbits and the like, as well as domestic animals and pets, such as cats and dogs, and even humans.

The infestation of fleas on domestic animals and pets likewise represents for the owner a problem which has not yet been satisfactorily resolved. Owing to their complex life cycle, none of the known methods for the control of fleas is completely satisfactory, especially as most known methods are basically directed towards the control of adult fleas in the pelt, and leave completely untouched the different juvenile stages of the fleas, which exist not only in the pelt of the animal, but also on the floor, in carpets, in the bedding of the animal, on chairs, in the garden and all other places with which the infested animal comes into contact. Flea treatment is usually expensive and has to be continued over long periods of time. Success usually depends on treating not only the infested animal, e.g. the dog or cat, but at the same time all the locations which the infested animal frequents.

The compounds of formula (I) according to the invention may be used alone or in combination with other biocides. They may be combined with pesticides having the same sphere of activity e.g. to increase activity, or with substances having another sphere of activity e.g. to broaden the range of activity. If the range of activity is to be extended to endoparasites, e.g. wormers, the compounds of formula (I) are suitably combined with substances having endoparasitic properties. Of course, they can also be used in combination with antibacterial compositions. Since the compounds of formula (I) are adulticides, i.e. since they are effective in particular against the adult stage of the target parasites, the addition of pesticides which instead attack the juvenile stages of the parasites may be very advantageous. In this way, the whole population spectrum of parasites is included, and in addition this contributes to substantially reducing the formation of resistance.

The good pesticidal activity of the compounds (I) according to the invention corresponds to a mortality rate of at least 50–60% of the pests mentioned.

The action of the compounds according to the invention and the compositions comprising them against animal pests can be significantly broadened and adapted to the given circumstances by the addition of other insecticides and/or acaricides. Suitable additives include, for example, representatives of the following classes of active ingredient: organophosphorus compounds, nitrophenols and derivatives, formamidines, thioureas, benzoylureas, carbamates, pyrethroids, neonicotinoids, chlorinated hydrocarbons and *Bacillus thuringiensis* preparations.

Especially suitable mixing partners are: Azamethiphos; Chlorfenvinphos; Cypermethrin, Cypermethrin high-cis; Cyromazin; Diafenthiuron; Diazinon; Dichlorvos; Dicrotophos; Dicyclanil; Fenoxycarb; Fluazuron; Furathiocarb; Isazofos; Jodfenphos; Kinoprene; Lufenuron; Methacriphos; Methidathion; Monocrotophos; Phosphamidon; Profenofos; Diofenolan; o compound obtainable from *Bacillus thuringiensis* strain $GC_{91}$ or from NCTC11821; Pymetrozine; Bromopropylate; Methoprene; Disulfuton; Quinalphos; Tau-Fluvalinate; Thiocyclam; Thiometon; Aldicarb; Azinphosmethyl; Benfuracarb; Bifenthrin; Buprofezin; Carbofuran; Cartap; Chlorfluazuron; Chlorpyrifos; Cyfluthrin; Lambda-Cyhalothrin; Alpha-cypermethrin; zeta-Cypermethrin; Deltamethrin; Diflubenzuron; Endosulfan; Ethiofencarb; Fenitrothion; Fenobucarb; Fenvalerate; Formothion; Methiocarb; Heptenophos; Imidacloprid; Isoprocarb; Methamidophos; Methomyl; Mevinphos; Parathion; Parathion-methyl; Phosalone; Pirimicarb; Propoxur; Teflubenzuron; Terbufos; Triazamate; Abamectin; Fenobucarb; Tebufenozide; Fipronil; beta-Cyfluthrin; Silafluofen, Fenpyroximate; Pyridaben; Fenazaquin; Pyriproxyfen; Pyrimidifen; Nitenpyram; NI-25, Acetamiprid; Avermectin $B_1$ (Abamectin); an insecticidally active extract of a plant; a preparation containing a nematocidally active component; a compound obtainable from *Bacillus subtilis*; a preparation containing insecticidally active fungi; a preparation containing an insecticidally active virus; AC303 630; Acephate; Acrinathrin; Alanycarb; Alphamethrin; Amitraz; AZ 60541; Azinphos A; Azinphos M; Azocyclotin; Bendiocarb; Bensultap; Betacyfluthrin; BPMC; Brofenprox; Bromophos A; Bufencarb; Butocarboxin; Butylpyridaben; Cadusafos; Carbaryl; Carbophenothion; Chloethocarb; Chlorethoxyfos; Chlormephos; Cis-Res-methrin; Clocythrin; Clofentezin; Cyanophos; Cycloprothrin; Cyhexatin; Demeton M; Demeton S; Demeton-S-methyl; Dichlofenthion; Dicliphos; Diethion; Dimethoat; Dimethylvinphos; Dioxathion; Edifenphos; Emamectin; Esfenvalerat; Ethion; Ethofenprox; Ethoprophos; Etrimphos; Fenamiphos; Fenbutatinoxid; Fenothiocarb; Fenpropathrin; Fenpyrad; Fenthion; Fluazinam; Flucycloxuron; Flucythrinat; Flufenoxuron; Flufenprox; Fonophos; Fosthiazat; Fubfenprox; HCH; Hexaflumuron; Hexythiazox; Iprobenfos; Isofenphos; Isoxathion; Ivermectin; Lambda-cyhalothrin; Malathion; Mecarbam; Mesulfenphos; Metaldehyd; Metolcarb; Milbemectin; Moxidectin; Naled; NC 184; Omethoat; Oxamyl; Oxydemethon M; Oxydeprofos; Permethrin; Phenthoat; Phorat; Phosmet; Phoxim; Pirimiphos M; Pirimiphos A; Promecarb; Propaphos; Prothiofos; Prothoat; Pyrachlophos; Pyradaphenthion; Pyresmethrin; Pyrethrum; RH 5992; Salithion; Sebufos; Sulfotep; Sulprofos; Tebufenpyrad; Tebupirimphos; Tefluthrin; Temephos; Terbam; Tetrachlor-vinphos; Thiacloprid; Thiamethoxam; Thiafenox; Thiodicarb; Thiofanox; Thionazin; Thuringiensin; Tralomethrin; Triarthen; Triazophos; Triazuron; Trichlorfon; Triflumuron; Trimethacarb; Vamidothion; Xylylcarb; YI 5301/5302; Zetamethrin; DPX-MP062; RH-2485; D 2341 or XMC (3,5,-Xy-lyl Methylcarbamate).

The compounds of formula (I) are preferably employed in unmodified form or preferably together with the adjuvants conventionally used in the art of formulation and may therefore be processed in a known manner to give, for example, emulsifiable concentrates, directly sprayable or dilutable solutions, dilute emulsions, wettable powders, soluble powders, dusts, granules or microencapsulations in polymeric substances.

The formulation, i.e. the agents, preparations or compositions containing the active ingredient of formula (I), or combinations of these active ingredients with other agrochemical active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants), and they likewise form an object of the invention.

The methods of application for the compositions, i.e. the methods of controlling pests of said type, such as spraying, atomizing, dusting, coating, dressing, scattering or pouring (chosen in accordance with the intended objectives and prevailing circumstances), and the use of the compositions for controlling pests of said type are further objects of the invention. Typical concentrations of active ingredient are between 0.1 and 1000 ppm, preferably between 0.1 and 500 ppm. The rates of application are generally 1 to 2000 g of active ingredient per hectare, especially 10 to 1000 g/ha, and preferably 20 to 600 g/ha.

A preferred method of application for crop protection is to apply the active ingredient to the foliage of the plants (leaf application), the number of applications and the rate of application depending on the intensity of infestation by the pest in question. However, the active ingredients can also penetrate the plant through the roots via the soil (systemic action) by impregnating the locus of the plant with a liquid composition, or by applying the compounds in solid form to the soil, e.g. in granular form (soil application). With paddy rice cultures, granules may be metered into the flooded paddy field.

The crop protection agents of the invention are also suitable for protecting vegetative reproductive material, e.g. seeds, such as fruits, tubers or grains, or plant seedlings, from animal pests. The reproductive material can be treated with the composition before the start of cultivation, seeds for example being dressed before they are sown. The active ingredients of the invention can also be applied to seeds (coating) by either soaking the seeds in a liquid composition or coating them with a solid composition. The composition can also be given when the reproductive material is introduced to the place of cultivation, e.g. when the seeds are sown in the seed furrow. The treatment procedures for vegetative reproductive material and the vegetative reproductive material thus treated are further objects of the invention.

The formulation, i.e. the agents, preparations or compositions containing the active ingredient of formula (I), or combinations of these active ingredients with other agrochemical active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants), and they likewise form an object of the invention.

The adjuvants which can be used for formulation are, for example, solid carriers, solvents, stabilizers, "slow-release" agents, dyes, and where appropriate surfactants. Carriers and adjuvants can be any substance conventionally used in crop protection agents. Adjuvants such as solvents, solid carriers, surface-active agents, non-ionic surfactants, cationic surfactants, anionic surfactants, and other adjuvants in the compositions of the invention can, for example, be the same as those described in EP-A-736'252, and are included by reference in the object of the present invention.

Suitable soaps are the alkali metal salts, alkaline earth metal salts or optionally substituted ammonium salts of higher fatty acids ($C_{10}$–$C_{22}$), for example the sodium or potassium salts of oleic or stearic acid, or of natural fatty acid mixtures which can be obtained for example from coconut oil or tallow oil. The fatty acid methyltaurin salts may also be mentioned as surfactants.

More frequently, however, so-called synthetic surfactants are used, especially fatty sulphonates, fatty sulphates, sulphonated benzimidazole derivatives or alkylarylsulphonates.

The fatty sulphonates or sulphates are usually in the form of alkali metal salts, alkaline earth metal salts or unsubstituted or substituted ammoniums salts and have an alkyl radical with 8 to 22 carbon atoms, which also includes the alkyl moiety of acyl radicals, for example, the sodium or calcium salt of lignonsulphonic acid, of dodecylsulphate or of a mixture of fatty alcohol sulphates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8–22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide or phospholipids.

The compounds of formula (I) are also notable inter alia for their excellent anti-flea activity, whereby not only are adult fleas rapidly killed, but via the roundabout route also the juvenile flea stages. Flea larvae that hatch from the flea eggs basically feed on the excretions of the adult fleas. Since the compounds of formula (I) according to the invention kill the adult fleas very rapidly, the necessary excretions which form the basis of food for the juvenile stages are missing, so that the latter are destroyed before they reach the adult stage.

A further preferred object of the present invention is thus a method for the control of parasites on humans, domestic animals, livestock and pets, consisting of a composition which contains at least one compound of formula (I), or a physiologically acceptable salt thereof, and is administered to the warm-blooded animal systemically or preferably topically in an effective dose.

Long-term activity is attained with various application forms of the compounds of formula (I) according to the invention, e.g. by administering the active substance in formulated form externally or internally to the animal requiring treatment. Formulated in this case means e.g. in the form of a powder, a tablet, a granulate, in liposomes, a capsule, an emulsion, a foam, a spray, in microencapsulated form, as pour-on, as spot-on. Of course, all compositions to be administered orally contain further additives, in addition to the usual formulation excipients, which encourage willing oral consumption by the host animal, e.g. suitable odorous substances, and flavourings and taste substances Percutaneous application, e.g. by subcutaneous or intramuscular injection or as a depot preparation in the form of an implant, or topical usage for example in the form of a pour-on or spot-on, represents one of the preferred objects of this invention because of the simplicity of application. A further type of application is oral application, e.g. in the form of a tablet. Percutaneous and topical application forms are of particular interest and show excellent results.

Percutaneous forms of administration include for example subcutaneous, intramuscular and even intravenous administration of injectable forms. Here, as well as the usual injection syringes with needles, needleless pressure systems can also be used.

Pour-on and spot-on formulations are preferred in particular as topical forms of application. Administration of sprays, ointments, solutions or powders may however also be expedient.

By choosing a suitable formulation, it is possible to enhance the penetration power of the active ingredients into the living tissue of the host animal, and to maintain its availability. This is important e.g. if rather poorly soluble active ingredients are used, the poor solubility requiring solubility-enhancing measures, since in these cases the body fluid of the animal can only dissolve small amounts of the active ingredients at a time.

Furthermore, a compound of formula (I) according to the invention may also be present in a matrix formulation in order to achieve a greatly delayed release of active ingredient. This matrix physically prevents release and premature secretion and maintains the bioavailability of the active ingredient. It is injected into the body e.g. intramuscularly or subcutaneously and remains there as a type of depot, from which the active ingredient is continuously released. Such matric formulations are known to the person skilled in the art. They are generally waxy, semi-solid substances, such as vegetable waxes and polyethylene glycols of high molecular weight, or solid polymer formulations, such as so-called microspheres.

The release rate of the active substance from the implant and thus the time-span during which the implant is active are generally determined by the accuracy of measurements (amount of active substance in the implant) of the implant, the surrounding environment of the implant and the polymer formulation from which the implant is produced.

The administration of veterinary medicine additives to animal food is best known in the field of animal health. Usually, first of all, a so-called premix is produced, in which the active substance is dispersed in a liquid or finely distributed in solid carriers. This premix can normally contain about 1 to 800 mg of the substance per kg, depending on the desired end concentration in the food.

Since the compounds of formula (I) according to the invention can be hydrolysed by constituents in the food, they should be formulated in a protective matrix, e.g. in gelatin, before adding to the premix.

The present invention thus also relates to the aspect of parasite control which is characterised by administering a compound of formula (I), which is protected against hydrolysis, to the host animal with the food.

The compound of formula (I) according to the invention is conveniently applied at a dosage of 0.01 to 800, preferably 0.1 to 200, especially 0.5 to 30 mg/kg body weight based on the host animal.

A good dosage that can be administered regularly to the host animal is between 0.5 and 100, preferably between 0.1 and 40 mg/kg body weight. Administration is carried out at suitable intervals, depending on the type of application and the body weight.

The total dose for the same active ingredient may vary from one species of animal to another and even within one species, since it depends inter alia on the weight, the age and the constitution of the host animal.

In the usage according to the invention, the compound of formula (I) according to the invention is normally not applied in pure form, but preferably in the form of a composition which contains, in addition to the active ingredient, application-enhancing constituents, whereby such constituents are beneficial to the host animal. Of course, in addition to controlling adult parasites according to the invention, the juvenile stages can be additionally controlled using conventional methods, but this is not absolutely necessary.

Such compositions to be used according to the invention usually contain 0.1 to 99% by weight, especially 0.1 to 95% by weight, of a compound of formula (I) according to the invention and 99.9 to 1% by weight, especially 99.9 to 5% by weight, of a solid or liquid, physiologically acceptable carrier, including 0 to 25% by weight, especially 0.1 to 25% by weight, or a non-toxic dispersant.

Whereas it is preferred to formulate commercial products as concentrates, the end user will normally use dilute formulations.

Such compositions may also contain further additives, such as stabilisers, anti-foaming agents, viscosity regulators, binding agents or tackifiers, as well as other active ingredients, in order to achieve special effects.

The formulation excipients which may be used are the physiologically acceptable carriers which are known from veterinary medicine for oral, percutaneous and topical administration. A few examples are mentioned hereinafter.

Suitable carriers are in particular fillers, such as sugars, e.g. lactose, saccharose, mannitol or sorbitol, cellulose preparations and/or calcium phosphates, e.g. tricalcium phosphate or calcium hydrogen phosphate, in a broader sense also binders, such as starch pastes using e.g. corn, wheat, rice or potato starch, gelatin, tragacanth, methyl cellulose and/or, if desired, disintegrants, such as the above-mentioned starches, in a broader sense also carboxymethyl starch, cross-linked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Tablet cores may be provided with suitable, where appropriate enteric, coatings, using inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavours or pigments may be added to the tablets or tablet coatings, for example for identification purposes or to indicate different doses of active ingredient.

Further orally administrable preparations include hard capsules consisting of gelatin, and also soft, sealed capsules consisting of gelatin and a plasticiser, such as glycerol or sorbitol. The hard capsules may contain the active ingredient in the form of granules, for example in admixture with fillers, such as lactose, binders, such as starches, and/or glidants, such as talc or magnesium stearate, and where appropriate stabilisers. In soft capsules, the active ingredient is preferably dissolved or suspended in suitable liquids, such as fatty oils, paraffin oil, or liquid polyethylene glycols, and stabilisers may likewise be added. Amongst other forms, capsules which can be both easily chewed and also swallowed whole are preferred.

The pour-on or spot-on method consists in applying the compound of formula (I) to a specific location of the skin or fur, advantageously to the neck or backbone of the animal. This takes place e.g. by applying a swab or spray of the pour-on or spot-on formulation to a relatively small area of the coat, from where the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$–$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are pyrrolidin-2-one, N-alkylpyrrolidin-2-one, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 20% by weight of a compound of formula (I), 0.1 to 50% by weight of dispersing agent and 45 to 98.9% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

For parenteral or percutaneous administration, oily injection solutions or suspensions are suitable, whereby suitable lipophilic solvents or vehicles are used, such as fatty oils, e.g. sesame oil, or synthetic fatty acid esters, e.g. ethyl oleate, or triglycerides, or aqueous injection solutions or suspensions are suitable. These contain viscosity-increasing substances, e.g. sodium carboxymethyl cellulose, sorbitol and/or dextran and optionally stabilisers.

The compositions of the present invention may be prepared in a manner known per se, for example by means of conventional mixing, granulating, coating, dissolving or lyophilising processes. Pharmaceutical compositions for oral administration can be obtained, for example, by combining the active ingredient with solid carriers, granulating a resulting mixture where appropriate, and processing the mixture or granules, if desired or if necessary following the addition of suitable excipients, to form tablets or tablet cores.

The following examples merely serve to illustrate the invention, without limiting the scope thereof.

Particularly preferred formulations are made up as follows:
(%=percent by weight)

| Emulsifiable concentrates: | |
|---|---|
| active ingredient: | 1 to 90%, preferably 5 to 20% |
| surfactant: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surf actant: | 0.5 to 20%, preferably 1 to 15% |
| solid carrier: | 5 to 95%, preferably 15 to 90% |
| Granulates: | |
| active ingredient: | 0.5 to 30%, preferably 3 to 15% |
| solid carrier: | 99.5 to 70%, preferably 97 to 85% |
| Injection solution: | |
| active ingredient: | 0.1 to 10%, preferably 0.5 to 5% |
| non-ionic surfactant mixture of ethanol and propylene glycol | 0.1 to 30%, preferably 0.5 to 10% |
| Injection suspension (aqueous or oily): | 60 to 99%, preferably 85 to 90% |
| active ingredient: | 0.1 to 20%, preferably 1 to 10% |
| non-ionic surfactant | 0.1 to 20%, preferably 1 to 10% |
| water or vegetable oil | 60 to 99%, preferably 85 to 95% |

The compositions may also contain further additives, such as stabilisers, e.g. where appropriate epoxidised vegetable oils (epoxidised coconut oil, rapeseed oil, or soybean oil); antifoams, typically silicone oil, preservatives, viscosity regulators, binders, and tackifiers, as well as fertilisers or other chemical agents to achieve special effects.

The following examples illustrate the above-described invention without limiting its scope in any way. Temperatures are given in degrees Celsius.

1. SYNTHESIS EXAMPLES

P1.2: 2,6-difluorophenyl-benzamidinium chloride 17.4 g of tert.-butyl hypochlorite are added dropwise to a solution of 26.1 g of 2,6-difluorobenzaldehyde oxime in 200 ml of methylene chloride in such a way that the temperature can be maintained at 20° C. After one hour, the reaction mixture is slowly added dropwise to 100 ml of a saturated methanolic ammonia solution. After a further hour, it is poured onto water, concentrated under vacuum, and the crystalline precipitate obtained is filtered and dried.

The hydroxamic acid amide thus obtained in 220 ml of hydrochloric-acid-containing ethanol is hydrogenated at 3 bars and at 60° C. over 9 g of Raney nickel. After filtering, concentrating under vacuum and recrystallising from ether, the title compound is obtained with a melting point of >250° C.

P1.2: 2-(4-bromophenyl)-1-dimethylamino-3-dimethylimmoniopropene Perchlorate 32 ml of phosphorus oxychloride are added dropwise at 10–15° C., with good cooling and intensive stirring, to 45 ml of dimethylformamide. Subsequently, 25 g of 4-bromophenylacetic acid are added in portions at −10° C., and the reaction mixture is stirred for 1 hour at room temperature, then for 2 hours at 60° C. and finally for 5 hours at 80° C. The mixture is then carefully hydrolysed with 20 ml of water at 0° C., and the product is precipitated by adding 35 ml of 70% perchloric acid. After filtering and recrystallising from acetone/ether, the title compound is obtained in the form of colourless crystals with a melting point of 160° C.

P1.3: 5-(4-bromophenyl)-2-(2,6-difluorophenyl)-pyrimidine

A suspension of 10.0 g of 2,6-difluorophenyl benzamidinium chloride and 19.0 g of 2-(4-bromophenyl)-1-dimethylamino-3-dimethylimmoniopropene perchlorate in 150 ml of methanol is mixed with 9.5 ml of a 5.4 molar NaOMe solution in methanol and heated for 16 hours under reflux. The cooled reaction mixture is subsequently poured onto water and the crystalline, colourless precipitate filtered. After drying under a high vacuum, the title compound is obtained with a melting point of 193–194° C.

P1.4: 2-(2,6-difluorophenyl)-5-(4'-trifluoromethoxybiphenyl-4-yl)-pyrimidine 0.70 g of 5-(4-bromophenyl)-2-(2,6-difluorophenyl)-pyrimidine, 0.53 g of 4-trifluoromethoxyphenyl-boric acid and 0.07 g of palladium-II-acetate are heated under reflux for 1½ hours, under nitrogen, in a mixture of 20 ml of dimethoxyethane and 20 ml of saturated, aqueous potassium carbonate solution. The reaction mixture is then cooled, diluted with water and the crystalline precipitate filtered. After dissolving the precipitate in ethyl acetate, drying with magnesium sulfate, filtering and concentrating, the title compound is obtained in the form of light yellow crystals with a melting point of 215–216° C.

P1.5: 4-(4-bromophenyl)-2-(2,6-difluorophenyl)-pyrimidine

A suspension of 10.0 g of 2,6-difluorophenyl-benzamidinium chloride and 10.4 g of 1-(4-bromophenyl)-3-dimethylaminopropenone in 100 ml of ethanol is mixed with 6.7 g of solid potassium tert.-butylate and heated under reflux for 16 hours. The cooled reaction mixture is poured onto water and the crystalline precipitate filtered. After recrystallising from ether/hexane, the title compound is obtained with a melting point of 130–131° C.

P1.6: 2-(2,6-difluorophenyl)-4-(4'-trifluoromethylbiphenyl-4-yl)-pyrimidine 0.70 g of 5-(4-bromophenyl)-2-(2,6-difluorophenyl)-pyrimidine, 0.42 g of 4-trifluoromethoxyphenyl-boric acid and 0.07 g of palladium-II-acetate are heated under reflux for 1½ hours, under nitrogen, in a mixture of 20 ml of dimethoxyethane and 20 ml of saturated, aqueous potassium carbonate solution. The reaction mixture is then cooled, diluted with water and the crystalline precipitate filtered. After dissolving the precipitate in ethyl acetate, drying with magnesium sulfate, filtering and concentrating, the title compound is obtained in the form of light yellow crystals with a melting point of 141–2° C.

P1.7: 4-(4-bromophenyl)-2-(2,6-difluorophenyl)-hydroxypyrimidine

A suspension of 750 ml of toluene, 24.0 g of 2,6-difluorophenyl-benzamidinium chloride and 31.9 g of 2-(4-bromophenyl)-3-hydroxyacrylic acid ethyl ester is mixed with 12.6 g of Triethylamine and 0.5 g of p-toluenesulfonic acid, and heated under reflux for 7 hours. The cooled reaction mixture is extracted with water and the solvent evaporated. After dissolving the precipitate in ethyl acetate, drying with magnesium sulfate, filtering and concentrating, the title compound is obtained with a melting point >250° C. (compound 3.356).

P1.8: 4-(4-bromophenyl)-2-(2,6-difluorophenyl)-3-chloropyrimidine 23.2 g of 4-(4-bromophenyl)-2-(2,6-difluorophenyl)-3-hydroxypyrimidine and 100 ml of $POCl_3$ are mixed and stirred for one hour at 110° C. The reaction mixture is slowly poured into a solution of 250 g of NaOH (solid) in water, and filtered. After dissolving the precipitate in ethyl acetate, drying with magnesium sulfate, filtering and concentrating, the title compound is obtained with a melting point of 146–148° C. (compound 3.354).

P1.9: 4-(4-bromophenyl)-3-cyano-2-(2,6-difluorophenyl)-pyrimidine 6 g of 4-(4-bromophenyl)-2-(2,6-difluorophenyl)-3-chloropyrimidine, 80 ml of dimethylformamide, 1.53 g of KCN and 0.93 g of sodium tolylsulfinate are mixed together, stirred for 3 hours at 80° C., mixed with ice water and filtered. After dissolving the precipitate in ethyl acetate, drying with magnesium sulfate, filtering and concentrating, the title compound is obtained with a melting point 146–148° C. (compound 3.355).

P1.10: 6 g of 4-(4-bromophenyl)-2-(2,6-difluorophenyl)-3-methoxypyrimidine 6 g of 4-(4-bromophenyl)-2-(2,6-difluorophenyl)-3-chloropyrimidine, 60 ml of methanol and 3.3 g of methanolic sodium methanolate solution (30%) are boiled under reflux for 24 hours, concentrated by evaporation, and the residue taken up in ethyl acetate and the organic phase washed with water. After drying with magnesium sulfate, filtering and concentrating, the title compound is obtained with a melting point of 104–106° C. (compound 3.350).

The substances named in the following tables may also be produced analogously to the methods described in examples P1.1 to P1.10.

TABLE 1

Compounds of the formula

| No. | $X_1$ | $X_2$ | $R_{21}$ | $R_a$ | $R_b$ | $R_c$ | $R_d$ | $R_e$ | m.p. (° C.) |
|---|---|---|---|---|---|---|---|---|---|
| 1.1 | F | F | H | H | Cl | F | H | H | 218–220 |
| 1.2 | F | F | H | H | H | $CF_3$ | H | H | 252–254 |
| 1.3 | Cl | Cl | H | H | H | $CF_3$ | H | H | 207–208 |
| 1.4 | Cl | Cl | H | H | H | $OCF_3$ | H | H | 179–181 |
| 1.5 | Cl | Cl | H | H | Cl | F | H | H | 200–202 |
| 1.6 | Cl | Cl | H | H | Cl | Cl | H | H | 224–226 |
| 1.7 | Cl | Cl | H | H | H | $OCH_3$ | H | H | 242–244 |
| 1.8 | Cl | Cl | H | H | H | Cl | H | H | 205–220 |
| 1.9 | Cl | Cl | H | H | Cl | H | Cl | H | >220 |
| 1.10 | Cl | Cl | H | H | H | t-Bu | H | H | 200–202 |
| 1.11 | Cl | F | H | H | Cl | F | H | H | 186–189 |
| 1.12 | Cl | F | H | H | H | $OCF_3$ | H | H | 160–163 |
| 1.13 | Cl | F | H | H | Cl | Cl | H | H | 196–199 |
| 1.14 | Cl | F | H | H | $CF_3$ | H | H | H | 187–190 |
| 1.15 | Cl | F | H | H | H | $OCH_3$ | H | H | 176–179 |
| 1.16 | Cl | F | H | H | Cl | H | Cl | H | 215–218 |

TABLE 1-continued

Compounds of the formula

| No. | $X_1$ | $X_2$ | $R_{21}$ | $R_a$ | $R_b$ | $R_c$ | $R_d$ | $R_e$ | m.p. (° C.) |
|---|---|---|---|---|---|---|---|---|---|
| 1.17 | Cl | F | H | H | H | $CF_3$ | H | H | 218–221 |
| 1.18 | F | F | H | H | $CF_3$ | H | H | H | 217–218 |
| 1.19 | F | F | H | H | H | $OCF_3$ | H | H | 215–216 |
| 1.20 | F | F | H | $OCH_3$ | H | H | H | H | 150–151 |
| 1.21 | F | F | H | H | Cl | H | Cl | H | 230–231 |
| 1.22 | F | F | H | H | H | Ph | H | H | >260 |
| 1.23 | F | F | H | H | H | F | H | H | 212–213 |
| 1.24 | F | F | H | $CF_3$ | H | H | H | H | 100–102 |
| 1.25 | F | F | H | H | H | Cl | H | H | 220–222 |
| 1.26 | F | F | CN | H | H | $OCF_3$ | H | H | 180–182 |
| 1.27 | F | F | CN | H | H | $CF_3$ | H | H | 199–201 |
| 1.28 | F | F | CN | H | Cl | H | Cl | H | 244–246 |
| 1.29 | F | F | $OCH_3$ | H | H | $OCF_3$ | H | H | 158–160 |
| 1.30 | F | F | $OCH_3$ | H | H | $CF_3$ | H | H | 176–178 |
| 1.31 | F | F | $OCH_3$ | H | Cl | H | Cl | H | 171–173 |
| 1.32 | F | F | $NHCH_3$ | H | H | $OCF_3$ | H | H | 196–197 |
| 1.33 | F | F | $NHCH_3$ | H | H | $CF_3$ | H | H | 214–216 |
| 1.34 | F | F | $NHCH_3$ | H | Cl | H | Cl | H | 270–272 |
| 1.35 | F | F | $SCH_3$ | H | H | $CF_3$ | H | H | 173–175 |
| 1.36 | F | F | Cl | H | H | $OCF_3$ | H | H | 177–179 |
| 1.37 | F | F | H | H | Cl | H | H | H | 178–179 |
| 1.38 | F | F | CN | H | H | $OCF_3$ | H | H | 180–182 |
| 1.39 | F | F | $OCH_3$ | H | H | $OCF_3$ | H | H | 158–160 |
| 1.40 | F | F | $OCH_3$ | H | H | $CF_3$ | H | H | 176–178 |
| 1.41 | F | F | $OCH_3$ | H | Cl | H | Cl | H | 171–173 |
| 1.42 | F | F | CN | H | H | $CF_3$ | H | H | 199–201 |
| 1.43 | F | F | CN | H | Cl | H | Cl | H | 244–246 |
| 1.44 | F | F | $NHCH_3$ | H | H | $OCF_3$ | H | H | 196–197 |
| 1.45 | F | F | $NHCH_3$ | H | H | $CF_3$ | H | H | 214–216 |
| 1.46 | F | F | $NHCH_3$ | H | Cl | H | Cl | H | 270–272 |
| 1.47 | F | F | H | H | H | $SCF_3$ | H | H | |
| 1.48 | F | F | H | H | H | $SOCF_3$ | H | H | |
| 1.49 | F | F | H | H | H | $SO2CF_3$ | H | H | |
| 1.50 | F | Cl | H | H | H | $SCF_3$ | H | H | |
| 1.51 | F | Cl | H | H | H | $SOCF_3$ | H | H | |
| 1.52 | F | Cl | H | H | H | $SO2CF_3$ | H | H | |
| 1.53 | Cl | Cl | H | H | H | $SCF_3$ | H | H | |
| 1.54 | Cl | Cl | H | H | H | $SOCF_3$ | H | H | |
| 1.55 | Cl | Cl | H | H | H | $SO2CF_3$ | H | H | |
| 1.56 | F | F | Cl | H | H | $OCF_3$ | H | H | 177–179 |
| 1.57 | F | F | —$SCH_3$ | H | H | $CF_3$ | H | H | 173–175 |
| 1.58 | F | F | —$OC_2H_5$ | H | H | $OCF_3$ | H | H | 146–147 |
| 1.59 | F | F | —$OC_2H_5$ | H | H | $CF_3$ | H | H | 170–172 |
| 1.60 | F | F | —$OC_2H_5$ | H | Cl | H | Cl | H | 154–155 |
| 1.61 | F | F | —O-i-Prop | H | H | $OCF_3$ | H | H | 128–129 |
| 1.62 | F | F | —NH-c-Prop | H | H | $OCF_3$ | H | H | 163–164 |
| 1.63 | F | F | —O-i-Prop | H | H | $CF_3$ | H | H | 159–160 |
| 1.64 | F | F | —O-i-Prop | H | Cl | H | Cl | H | 143–144 |
| 1.65 | F | F | —NH-c-Prop | H | H | $CF_3$ | H | H | 187–188 |
| 1.66 | F | F | —NH-c-Prop | H | Cl | H | Cl | H | 172–173 |
| 1.67 | F | F | —$NHC_2H_5$ | H | H | $CF_3$ | H | H | 189–190 |
| 1.68 | F | F | —$NHC_2H_5$ | H | Cl | H | Cl | H | 202–203 |
| 1.69 | F | F | —$N(CH_3)_2$ | H | H | $OCF_3$ | H | H | 146–147 |
| 1.70 | F | F | —$N(CH_3)_2$ | H | H | $CF_3$ | H | H | 166–168 |
| 1.71 | F | F | —$N(CH_3)_2$ | H | Cl | H | Cl | H | 200–202 |
| 1.72 | F | F | —$SC_2H_5$ | H | H | $OCF_3$ | H | H | 127–128 |
| 1.73 | F | F | —$SC_2H_5$ | H | H | $CF_3$ | H | H | 145–146 |
| 1.74 | F | F | —$SC_2H_5$ | H | Cl | H | Cl | H | 154–156 |

TABLE 2

Compounds of the formula

| No. | $X_1$ | $X_2$ | $R_x$ | $R_a$ | $R_b$ | $R_c$ | $R_d$ | $R_e$ | m.p. (° C.) |
|---|---|---|---|---|---|---|---|---|---|
| 2.1 | F | F | H | H | Cl | F | H | H | 133–134 |
| 2.2 | F | F | H | H | H | $CF_3$ | H | H | 141–142 |
| 2.3 | F | F | H | H | H | $OCF_3$ | H | H | 102–103 |
| 2.4 | F | F | H | H | $CF_3$ | H | H | H | 114–115 |
| 2.5 | F | F | H | H | Cl | H | Cl | H | 116–126 |
| 2.6 | F | F | H | H | Cl | Cl | H | H | 134–140 |
| 2.7 | F | F | H | H | H | Ph | H | H | 258–259 |
| 2.8 | F | F | H | H | H | F | H | H | 145–146 |
| 2.9 | F | F | H | Cl | H | Cl | H | H | 86–87 |
| 2.10 | F | F | H | H | Cl | H | H | H | 82–83 |
| 2.11 | F | F | H | H | H | Cl | H | H | 167–168 |
| 2.12 | F | F | H | $CF_3$ | H | H | H | H | 179–180 |

TABLE 3

Compounds of the formula

| No. | $X_1$ | $X_2$ | $R_{21}$ | $R_a$ | $R_c$ | phys. data |
|---|---|---|---|---|---|---|
| 3.1 | F | F | H | $CH_3$ | 4-F—Ph | |
| 3.2 | F | F | H | $CH_3$ | 4-Cl—Ph | |
| 3.3 | F | F | H | $CH_3$ | 3-$CF_3$—Ph | |
| 3.4 | F | F | H | $CH_3$ | 4-$CF_3$—Ph | |
| 3.5 | F | F | H | $CH_3$ | 4-$OCF_3$—Ph | |
| 3.6 | F | F | H | $CH_3$ | 4-t-Butyl-Ph | |
| 3.7 | F | F | H | $CH_3$ | 2,4-$Cl_2$—Ph | |
| 3.8 | F | F | H | $CH_3$ | 3,5-$Cl_2$—Ph | |
| 3.9 | F | F | H | $CH_3$ | 2-$CF_3$—Ph | |
| 3.10 | F | F | H | $CH_3$ | 4-$OCH_3$—Ph | |
| 3.11 | F | F | H | $CH_3$ | 4-$SCH_3$—Ph | |
| 3.12 | F | F | H | $CH_3$ | 3-$OCH_3$—Ph | |
| 3.13 | F | F | H | $CH_3$ | 3-Cl—Ph | |
| 3.14 | F | F | H | $CH_3$ | 3,4-$Cl_2$—Ph | |
| 3.15 | F | F | H | $CH_3$ | 3-Cl-4-F—Ph | |
| 3.16 | F | F | H | $CH_3$ | 4-Br | |
| 3.17 | F | F | H | $OCH_3$ | 4-F—Ph | |
| 3.18 | F | F | H | $OCH_3$ | 4-Cl—Ph | |
| 3.19 | F | F | H | $OCH_3$ | 3-$CF_3$—Ph | |
| 3.20 | F | F | H | $OCH_3$ | 4-$CF_3$—Ph | |
| 3.21 | F | F | H | $OCH_3$ | 4-$OCF_3$—Ph | |
| 3.22 | F | F | H | $OCH_3$ | 4-t-Butyl-Ph | |
| 3.23 | F | F | H | $OCH_3$ | 2,4-$Cl_2$—Ph | |
| 3.24 | F | F | H | $OCH_3$ | 3,5-$Cl_2$—Ph | |
| 3.25 | F | F | H | $OCH_3$ | 2-$CF_3$—Ph | |
| 3.26 | F | F | H | $OCH_3$ | 4-$OCH_3$—Ph | |
| 3.27 | F | F | H | $OCH_3$ | 4-$SCH_3$—Ph | |
| 3.28 | F | F | H | $OCH_3$ | 3-$OCH_3$—Ph | |
| 3.29 | F | F | H | $OCH_3$ | 3-Cl—Ph | |
| 3.30 | F | F | H | $OCH_3$ | 3,4-$Cl_2$—Ph | |
| 3.31 | F | F | H | $OCH_3$ | 3-Cl-4-F—Ph | |
| 3.32 | F | F | H | $CF_3$ | 4-F—Ph | |
| 3.33 | F | F | H | $CF_3$ | 4-Cl—Ph | |
| 3.34 | F | F | H | $CF_3$ | 3-$CF_3$—Ph | |
| 3.35 | F | F | H | $CF_3$ | 4-$CF_3$—Ph | |
| 3.36 | F | F | H | $CF_3$ | 4-$OCF_3$—Ph | |
| 3.37 | F | F | H | $CF_3$ | 4-t-Butyl-Ph | |
| 3.38 | F | F | H | $CF_3$ | 2,4-$Cl_2$—Ph | |
| 3.39 | F | F | H | $CF_3$ | 3,5-$Cl_2$—Ph | |
| 3.40 | F | F | H | $CF_3$ | 2-$CF_3$—Ph | |
| 3.41 | F | F | H | $CF_3$ | 4-$OCH_3$—Ph | |
| 3.42 | F | F | H | $CF_3$ | 4-$SCH_3$—Ph | |
| 3.43 | F | F | H | $CF_3$ | 3-$OCH_3$—Ph | |
| 3.44 | F | F | H | $CF_3$ | 3-Cl—Ph | |
| 3.45 | F | F | H | $CF_3$ | 3,4-$Cl_2$—Ph | |
| 3.46 | F | F | H | $CF_3$ | 3-Cl-4-F—Ph | |
| 3.47 | F | F | $CH_3$ | H | 4-F—Ph | |
| 3.48 | F | F | $CH_3$ | H | 4-Cl—Ph | |
| 3.49 | F | F | $CH_3$ | H | 3-$CF_3$—Ph | |
| 3.50 | F | F | $CH_3$ | H | 4-$CF_3$—Ph | |
| 3.51 | F | F | $CH_3$ | H | 4-$OCF_3$—Ph | |
| 3.52 | F | F | $CH_3$ | H | 4-t-Butyl-Ph | |
| 3.53 | F | F | $CH_3$ | H | 2,4-$Cl_2$—Ph | |
| 3.54 | F | F | $CH_3$ | H | 3,5-$Cl_2$—Ph | |
| 3.55 | F | F | $CH_3$ | H | 2-$CF_3$—Ph | |
| 3.56 | F | F | $CH_3$ | H | 4-$OCH_3$—Ph | |
| 3.57 | F | F | $CH_3$ | H | 4-$SCH_3$—Ph | |
| 3.58 | F | F | $CH_3$ | H | 3-$OCH_3$—Ph | |
| 3.59 | F | F | $CH_3$ | H | 3-Cl—Ph | |
| 3.60 | F | F | $CH_3$ | H | 3,4-$Cl_2$—Ph | |
| 3.61 | F | F | $CH_3$ | H | 3-Cl-4-F—Ph | |
| 3.62 | F | F | $CH_3$ | $CH_3$ | 4-F—Ph | |
| 3.63 | F | F | $CH_3$ | $CH_3$ | 4-Cl—Ph | |
| 3.64 | F | F | $CH_3$ | $CH_3$ | 3-$CF_3$—Ph | |
| 3.65 | F | F | $CH_3$ | $CH_3$ | 4-$CF_3$—Ph | |
| 3.66 | F | F | $CH_3$ | $CH_3$ | 4-$OCF_3$—Ph | |
| 3.67 | F | F | $CH_3$ | $CH_3$ | 4-t-Butyl-Ph | |
| 3.68 | F | F | $CH_3$ | $CH_3$ | 2,4-$Cl_2$—Ph | |
| 3.69 | F | F | $CH_3$ | $CH_3$ | 3,5-$Cl_2$—Ph | |
| 3.70 | F | F | $CH_3$ | $CH_3$ | 2-$CF_3$—Ph | |
| 3.71 | F | F | $CH_3$ | $CH_3$ | 4-$OCH_3$—Ph | |
| 3.72 | F | F | $CH_3$ | $CH_3$ | 4-$SCH_3$—Ph | |
| 3.73 | F | F | $CH_3$ | $CH_3$ | 3-$OCH_3$—Ph | |
| 3.74 | F | F | $CH_3$ | $CH_3$ | 3-Cl—Ph | |
| 3.75 | F | F | $CH_3$ | $CH_3$ | 3,4-$Cl_2$—Ph | |
| 3.76 | F | F | $CH_3$ | $CH_3$ | 3-Cl-4-F—Ph | |
| 3.77 | F | F | $CH_3$ | $OCH_3$ | 4-F—Ph | |
| 3.78 | F | F | $CH_3$ | $OCH_3$ | 4-Cl—Ph | |
| 3.79 | F | F | $CH_3$ | $OCH_3$ | 3-$CF_3$—Ph | |
| 3.80 | F | F | $CH_3$ | $OCH_3$ | 4-$CF_3$—Ph | |
| 3.81 | F | F | $CH_3$ | $OCH_3$ | 4-$OCF_3$—Ph | |
| 3.82 | F | F | $CH_3$ | $OCH_3$ | 4-t-Butyl-Ph | |
| 3.83 | F | F | $CH_3$ | $OCH_3$ | 2,4-$Cl_2$—Ph | |
| 3.84 | F | F | $CH_3$ | $OCH_3$ | 3,5-$Cl_2$—Ph | |
| 3.85 | F | F | $CH_3$ | $OCH_3$ | 2-$CF_3$—Ph | |
| 3.86 | F | F | $CH_3$ | $OCH_3$ | 4-$OCH_3$—Ph | |
| 3.87 | F | F | $CH_3$ | $OCH_3$ | 4-$SCH_3$—Ph | |
| 3.88 | F | F | $CH_3$ | $OCH_3$ | 3-$OCH_3$—Ph | |
| 3.89 | F | F | $CH_3$ | $OCH_3$ | 3-Cl—Ph | |
| 3.90 | F | F | $CH_3$ | $OCH_3$ | 3,4-$Cl_2$—Ph | |
| 3.91 | F | F | $CH_3$ | $OCH_3$ | 3-Cl-4-F—Ph | |
| 3.92 | F | F | $CH_3$ | $CF_3$ | 4-F—Ph | |
| 3.93 | F | F | $CH_3$ | $CF_3$ | 4-Cl—Ph | |
| 3.94 | F | F | $CH_3$ | $CF_3$ | 3-$CF_3$—Ph | |
| 3.95 | F | F | $CH_3$ | $CF_3$ | 4-$CF_3$—Ph | |
| 3.96 | F | F | $CH_3$ | $CF_3$ | 4-$OCF_3$—Ph | |
| 3.97 | F | F | $CH_3$ | $CF_3$ | 4-t-Butyl-Ph | |

TABLE 3-continued

Compounds of the formula

| No. | X₁ | X₂ | R₂₁ | Rₐ | R_c | phys. data |
|---|---|---|---|---|---|---|
| 3.98 | F | F | CH₃ | CF₃ | 2,4-Cl₂—Ph | |
| 3.99 | F | F | CH₃ | CF₃ | 3,5-Cl₂—Ph | |
| 3.100 | F | F | CH₃ | CF₃ | 2-CF₃—Ph | |
| 3.101 | F | F | CH₃ | CF₃ | 4-OCH₃—Ph | |
| 3.102 | F | F | CH₃ | CF₃ | 4-SCH₃—Ph | |
| 3.103 | F | F | CH₃ | CF₃ | 3-OCH₃—Ph | |
| 3.104 | F | F | CH₃ | CF₃ | 3-Cl—Ph | |
| 3.105 | F | F | CH₃ | CF₃ | 3,4-Cl₂—Ph | |
| 3.106 | F | F | CH₃ | CF₃ | 3-Cl-4-F—Ph | |
| 3.107 | F | Cl | H | H | 4-F—Ph | |
| 3.108 | F | Cl | H | H | 4-Cl—Ph | |
| 3.109 | F | Cl | H | H | 3-CF₃—Ph | |
| 3.110 | F | Cl | H | H | 4-CF₃—Ph | |
| 3.111 | F | Cl | H | H | 4-OCF₃—Ph | |
| 3.112 | F | Cl | H | H | 4-t-Butyl-Ph | |
| 3.113 | F | Cl | H | H | 2,4-Cl₂—Ph | |
| 3.114 | F | Cl | H | H | 3,5-Cl₂—Ph | |
| 3.115 | F | Cl | H | H | 2-CF₃—Ph | |
| 3.116 | F | Cl | H | H | 4-OCH₃—Ph | |
| 3.117 | F | Cl | H | H | 4-SCH₃—Ph | |
| 3.118 | F | Cl | H | H | 3-OCH₃—Ph | |
| 3.119 | F | Cl | H | H | 3-Cl—Ph | |
| 3.120 | F | Cl | H | H | 3,4-Cl₂—Ph | |
| 3.121 | F | Cl | H | H | 3-Cl-4-F—Ph | |
| 3.122 | F | Cl | H | CH₃ | 4-F—Ph | |
| 3.123 | F | Cl | H | CH₃ | 4-Cl—Ph | |
| 3.124 | F | Cl | H | CH₃ | 3-CF₃—Ph | |
| 3.125 | F | Cl | H | CH₃ | 4-CF₃—Ph | |
| 3.126 | F | Cl | H | CH₃ | 4-OCF₃—Ph | |
| 3.127 | F | Cl | H | CH₃ | 4-t-Butyl-Ph | |
| 3.128 | F | Cl | H | CH₃ | 2,4-Cl₂—Ph | |
| 3.129 | F | Cl | H | CH₃ | 3,5-Cl₂—Ph | |
| 3.130 | F | Cl | H | CH₃ | 2-CF₃—Ph | |
| 3.131 | F | Cl | H | CH₃ | 4-OCH₃—Ph | |
| 3.132 | F | Cl | H | CH₃ | 4-SCH₃—Ph | |
| 3.133 | F | Cl | H | CH₃ | 3-OCH₃—Ph | |
| 3.134 | F | Cl | H | CH₃ | 3-Cl—Ph | |
| 3.135 | F | Cl | H | CH₃ | 3,4-Cl₂—Ph | |
| 3.136 | F | Cl | H | CH₃ | 3-Cl-4-F—Ph | |
| 3.137 | F | Cl | H | OCH₃ | 4-F—Ph | |
| 3.138 | F | Cl | H | OCH₃ | 4-Cl—Ph | |
| 3.139 | F | Cl | H | OCH₃ | 3-CF₃—Ph | |
| 3.140 | F | Cl | H | OCH₃ | 4-CF₃—Ph | |
| 3.141 | F | Cl | H | OCH₃ | 4-OCF₃—Ph | |
| 3.142 | F | Cl | H | OCH₃ | 4-t-Butyl-Ph | |
| 3.143 | F | Cl | H | OCH₃ | 2,4-Cl₂—Ph | |
| 3.144 | F | Cl | H | OCH₃ | 3,5-Cl₂—Ph | |
| 3.145 | F | Cl | H | OCH₃ | 2-CF₃—Ph | |
| 3.146 | F | Cl | H | OCH₃ | 4-OCH₃—Ph | |
| 3.147 | F | Cl | H | OCH₃ | 4-SCH₃—Ph | |
| 3.148 | F | Cl | H | OCH₃ | 3-OCH₃—Ph | |
| 3.149 | F | Cl | H | OCH₃ | 3-Cl—Ph | |
| 3.150 | F | Cl | H | OCH₃ | 3,4-Cl₂—Ph | |
| 3.151 | F | Cl | H | OCH₃ | 3-Cl-4-F—Ph | |
| 3.152 | F | Cl | H | CF₃ | 4-F—Ph | |
| 3.153 | F | Cl | H | CF₃ | 4-Cl—Ph | |
| 3.154 | F | Cl | H | CF₃ | 3-CF₃—Ph | |
| 3.155 | F | Cl | H | CF₃ | 4-CF₃—Ph | |
| 3.156 | F | Cl | H | CF₃ | 4-OCF₃—Ph | |
| 3.157 | F | Cl | H | CF₃ | 4-t-Butyl-Ph | |
| 3.158 | F | Cl | H | CF₃ | 2,4-Cl₂—Ph | |
| 3.159 | F | Cl | H | CF₃ | 3,5-Cl₂—Ph | |
| 3.160 | F | Cl | H | CF₃ | 2-CF₃—Ph | |
| 3.161 | F | Cl | H | CF₃ | 4-OCH₃—Ph | |
| 3.162 | F | Cl | H | CF₃ | 4-SCH₃—Ph | |
| 3.163 | F | Cl | H | CF₃ | 3-OCH₃—Ph | |
| 3.164 | F | Cl | H | CF₃ | 3-Cl—Ph | |
| 3.165 | F | Cl | H | CF₃ | 3,4-Cl₂—Ph | |
| 3.166 | F | Cl | H | CF₃ | 3-Cl-4-F—Ph | |
| 3.167 | F | Cl | CH₃ | H | 4-F—Ph | |
| 3.168 | F | Cl | CH₃ | H | 4-Cl—Ph | |
| 3.169 | F | Cl | CH₃ | H | 3-CF₃—Ph | |
| 3.170 | F | Cl | CH₃ | H | 4-CF₃—Ph | |
| 3.171 | F | Cl | CH₃ | H | 4-OCF₃—Ph | |
| 3.172 | F | Cl | CH₃ | H | 4-t-Butyl-Ph | |
| 3.173 | F | Cl | CH₃ | H | 2,4-Cl₂—Ph | |
| 3.174 | F | Cl | CH₃ | H | 3,5-Cl₂—Ph | |
| 3.175 | F | Cl | CH₃ | H | 2-CF₃—Ph | |
| 3.176 | F | Cl | CH₃ | H | 4-OCH₃—Ph | |
| 3.177 | F | Cl | CH₃ | H | 4-SCH₃—Ph | |
| 3.178 | F | Cl | CH₃ | H | 3-OCH₃—Ph | |
| 3.179 | F | Cl | CH₃ | H | 3-Cl—Ph | |
| 3.180 | F | Cl | CH₃ | H | 3,4-Cl₂—Ph | |
| 3.181 | F | Cl | CH₃ | H | 3-Cl-4-F—Ph | |
| 3.182 | F | Cl | CH₃ | CH₃ | 4-F—Ph | |
| 3.183 | F | Cl | CH₃ | CH₃ | 4-Cl—Ph | |
| 3.184 | F | Cl | CH₃ | CH₃ | 3-CF₃—Ph | |
| 3.185 | F | Cl | CH₃ | CH₃ | 4-CF₃—Ph | |
| 3.186 | F | Cl | CH₃ | CH₃ | 4-OCF₃—Ph | |
| 3.187 | F | Cl | CH₃ | CH₃ | 4-t-Butyl-Ph | |
| 3.188 | F | Cl | CH₃ | CH₃ | 2,4-Cl₂—Ph | |
| 3.189 | F | Cl | CH₃ | CH₃ | 3,5-Cl₂—Ph | |
| 3.190 | F | Cl | CH₃ | CH₃ | 2-CF₃—Ph | |
| 3.191 | F | Cl | CH₃ | CH₃ | 4-OCH₃—Ph | |
| 3.192 | F | Cl | CH₃ | CH₃ | 4-SCH₃—Ph | |
| 3.193 | F | Cl | CH₃ | CH₃ | 3-OCH₃—Ph | |
| 3.194 | F | Cl | CH₃ | CH₃ | 3-Cl—Ph | |
| 3.195 | F | Cl | CH₃ | CH₃ | 3,4-Cl₂—Ph | |
| 3.196 | F | Cl | CH₃ | CH₃ | 3-Cl-4-F—Ph | |
| 3.197 | F | Cl | CH₃ | OCH₃ | 4-F—Ph | |
| 3.198 | F | Cl | CH₃ | OCH₃ | 4-Cl—Ph | |
| 3.199 | F | Cl | CH₃ | OCH₃ | 3-CF₃—Ph | |
| 3.200 | F | Cl | CH₃ | OCH₃ | 4-CF₃—Ph | |
| 3.201 | F | Cl | CH₃ | OCH₃ | 4-OCF₃—Ph | |
| 3.202 | F | Cl | CH₃ | OCH₃ | 4-t-Butyl-Ph | |
| 3.203 | F | Cl | CH₃ | OCH₃ | 2,4-Cl₂—Ph | |
| 3.204 | F | Cl | CH₃ | OCH₃ | 3,5-Cl₂—Ph | |
| 3.205 | F | Cl | CH₃ | OCH₃ | 2-CF₃—Ph | |
| 3.206 | F | Cl | CH₃ | OCH₃ | 4-OCH₃—Ph | |
| 3.207 | F | Cl | CH₃ | OCH₃ | 4-SCH₃—Ph | |
| 3.208 | F | Cl | CH₃ | OCH₃ | 3-OCH₃—Ph | |
| 3.209 | F | Cl | CH₃ | OCH₃ | 3-Cl—Ph | |
| 3.210 | F | Cl | CH₃ | OCH₃ | 3,4-Cl₂—Ph | |
| 3.211 | F | Cl | CH₃ | OCH₃ | 3-Cl-4-F—Ph | |
| 3.212 | F | Cl | CH₃ | CF₃ | 4-F—Ph | |
| 3.213 | F | Cl | CH₃ | CF₃ | 4-Cl—Ph | |
| 3.214 | F | Cl | CH₃ | CF₃ | 3-CF₃—Ph | |
| 3.215 | F | Cl | CH₃ | CF₃ | 4-CF₃—Ph | |
| 3.216 | F | Cl | CH₃ | CF₃ | 4-OCF₃—Ph | |
| 3.217 | F | Cl | CH₃ | CF₃ | 4-t-Butyl-Ph | |
| 3.218 | F | Cl | CH₃ | CF₃ | 2,4-Cl₂—Ph | |
| 3.219 | F | Cl | CH₃ | CF₃ | 3,5-Cl₂—Ph | |
| 3.220 | F | Cl | CH₃ | CF₃ | 2-CF₃—Ph | |
| 3.221 | F | Cl | CH₃ | CF₃ | 4-OCH₃—Ph | |
| 3.222 | F | Cl | CH₃ | CF₃ | 4-SCH₃—Ph | |
| 3.223 | F | Cl | CH₃ | CF₃ | 3-OCH₃—Ph | |
| 3.224 | F | Cl | CH₃ | CF₃ | 3-Cl—Ph | |
| 3.225 | F | Cl | CH₃ | CF₃ | 3,4-Cl₂—Ph | |
| 3.226 | F | Cl | CH₃ | CF₃ | 3-Cl-4-F—Ph | |
| 3.227 | Cl | Cl | H | H | 4-F—Ph | |

TABLE 3-continued

Compounds of the formula

| No. | X₁ | X₂ | R₂₁ | Rₐ | R_c | phys. data |
|---|---|---|---|---|---|---|
| 3.228 | Cl | Cl | H | H | 4-Cl—Ph | |
| 3.229 | Cl | Cl | H | H | 3-CF₃—Ph | |
| 3.230 | Cl | Cl | H | H | 4-CF₃—Ph | |
| 3.231 | Cl | Cl | H | H | 4-OCF₃—Ph | |
| 3.232 | Cl | Cl | H | H | 4-t-Butyl-Ph | |
| 3.233 | Cl | Cl | H | H | 2,4-Cl₂—Ph | |
| 3.234 | Cl | Cl | H | H | 3,5-Cl₂—Ph | |
| 3.235 | Cl | Cl | H | H | 2-CF₃—Ph | |
| 3.236 | Cl | Cl | H | H | 4-OCH₃—Ph | |
| 3.237 | Cl | Cl | H | H | 4-SCH₃—Ph | |
| 3.238 | Cl | Cl | H | H | 3-OCH₃—Ph | |
| 3.239 | Cl | Cl | H | H | 3-Cl—Ph | |
| 3.240 | Cl | Cl | H | H | 3,4-Cl₂—Ph | |
| 3.241 | Cl | Cl | H | H | 3-Cl-4-F—Ph | |
| 3.242 | Cl | Cl | H | CH₃ | 4-F—Ph | |
| 3.243 | Cl | Cl | H | CH₃ | 4-Cl—Ph | |
| 3.244 | Cl | Cl | H | CH₃ | 3-CF₃—Ph | |
| 3.245 | Cl | Cl | H | CH₃ | 4-CF₃—Ph | |
| 3.246 | Cl | Cl | H | CH₃ | 4-OCF₃—Ph | |
| 3.247 | Cl | Cl | H | CH₃ | 4-t-Butyl-Ph | |
| 3.248 | Cl | Cl | H | CH₃ | 2,4-Cl₂—Ph | |
| 3.249 | Cl | Cl | H | CH₃ | 3,5-Cl₂—Ph | |
| 3.250 | Cl | Cl | H | CH₃ | 2-CF₃—Ph | |
| 3.251 | Cl | Cl | H | CH₃ | 4-OCH₃—Ph | |
| 3.252 | Cl | Cl | H | CH₃ | 4-SCH₃—Ph | |
| 3.253 | Cl | Cl | H | CH₃ | 3-OCH₃—Ph | |
| 3.254 | Cl | Cl | H | CH₃ | 3-Cl—Ph | |
| 3.255 | Cl | Cl | H | CH₃ | 3,4-Cl₂—Ph | |
| 3.256 | Cl | Cl | H | CH₃ | 3-Cl-4-F—Ph | |
| 3.257 | Cl | Cl | H | OCH₃ | 4-F—Ph | |
| 3.258 | Cl | Cl | H | OCH₃ | 4-Cl—Ph | |
| 3.259 | Cl | Cl | H | OCH₃ | 3-CF₃—Ph | |
| 3.260 | Cl | Cl | H | OCH₃ | 4-CF₃—Ph | |
| 3.261 | Cl | Cl | H | OCH₃ | 4-OCF₃—Ph | |
| 3.262 | Cl | Cl | H | OCH₃ | 4-t-Butyl-Ph | |
| 3.263 | Cl | Cl | H | OCH₃ | 2,4-Cl₂—Ph | |
| 3.264 | Cl | Cl | H | OCH₃ | 3,5-Cl₂—Ph | |
| 3.265 | Cl | Cl | H | OCH₃ | 2-CF₃—Ph | |
| 3.266 | Cl | Cl | H | OCH₃ | 4-OCH₃—Ph | |
| 3.267 | Cl | Cl | H | OCH₃ | 4-SCH₃—Ph | |
| 3.268 | Cl | Cl | H | OCH₃ | 3-OCH₃—Ph | |
| 3.269 | Cl | Cl | H | OCH₃ | 3-Cl—Ph | |
| 3.270 | Cl | Cl | H | OCH₃ | 3,4-Cl₂—Ph | |
| 3.271 | Cl | Cl | H | OCH₃ | 3-Cl-4-F—Ph | |
| 3.272 | Cl | Cl | H | CF₃ | 4-F—Ph | |
| 3.273 | Cl | Cl | H | CF₃ | 4-Cl—Ph | |
| 3.274 | Cl | Cl | H | CF₃ | 3-CF₃—Ph | |
| 3.275 | Cl | Cl | H | CF₃ | 4-CF₃—Ph | |
| 3.276 | Cl | Cl | H | CF₃ | 4-OCF₃—Ph | |
| 3.277 | Cl | Cl | H | CF₃ | 4-t-Butyl-Ph | |
| 3.278 | Cl | Cl | H | CF₃ | 2,4-Cl₂—Ph | |
| 3.279 | Cl | Cl | H | CF₃ | 3,5-Cl₂—Ph | |
| 3.280 | Cl | Cl | H | CF₃ | 2-CF₃—Ph | |
| 3.281 | Cl | Cl | H | CF₃ | 4-OCH₃—Ph | |
| 3.282 | Cl | Cl | H | CF₃ | 4-SCH₃—Ph | |
| 3.283 | Cl | Cl | H | CF₃ | 3-OCH₃—Ph | |
| 3.284 | Cl | Cl | H | CF₃ | 3-Cl—Ph | |
| 3.285 | Cl | Cl | H | CF₃ | 3,4-Cl₂—Ph | |
| 3.286 | Cl | Cl | H | CF₃ | 3-Cl-4-F—Ph | |
| 3.287 | Cl | Cl | CH₃ | H | 4-F—Ph | |
| 3.288 | Cl | Cl | CH₃ | H | 4-Cl—Ph | |
| 3.289 | Cl | Cl | CH₃ | H | 3-CF₃—Ph | |
| 3.290 | Cl | Cl | CH₃ | H | 4-CF₃—Ph | |
| 3.291 | Cl | Cl | CH₃ | H | 4-OCF₃—Ph | |
| 3.292 | Cl | Cl | CH₃ | H | 4-t-Butyl-Ph | |
| 3.293 | Cl | Cl | CH₃ | H | 2,4-Cl₂—Ph | |
| 3.294 | Cl | Cl | CH₃ | H | 3,5-Cl₂—Ph | |
| 3.295 | Cl | Cl | CH₃ | H | 2-CF₃—Ph | |
| 3.296 | Cl | Cl | CH₃ | H | 4-OCH₃—Ph | |
| 3.297 | Cl | Cl | CH₃ | H | 4-SCH₃—Ph | |
| 3.298 | Cl | Cl | CH₃ | H | 3-OCH₃—Ph | |
| 3.299 | Cl | Cl | CH₃ | H | 3-Cl—Ph | |
| 3.300 | Cl | Cl | CH₃ | H | 3,4-Cl₂—Ph | |
| 3.301 | Cl | Cl | CH₃ | H | 3-Cl-4-F—Ph | |
| 3.302 | Cl | Cl | CH₃ | CH₃ | 4-F—Ph | |
| 3.303 | Cl | Cl | CH₃ | CH₃ | 4-Cl—Ph | |
| 3.304 | Cl | Cl | CH₃ | CH₃ | 3-CF₃—Ph | |
| 3.305 | Cl | Cl | CH₃ | CH₃ | 4-CF₃—Ph | |
| 3.306 | Cl | Cl | CH₃ | CH₃ | 4-OCF₃—Ph | |
| 3.307 | Cl | Cl | CH₃ | CH₃ | 4-t-Butyl-Ph | |
| 3.308 | Cl | Cl | CH₃ | CH₃ | 2,4-Cl₂—Ph | |
| 3.309 | Cl | Cl | CH₃ | CH₃ | 3,5-Cl₂—Ph | |
| 3.310 | Cl | Cl | CH₃ | CH₃ | 2-CF₃—Ph | |
| 3.311 | Cl | Cl | CH₃ | CH₃ | 4-OCH₃—Ph | |
| 3.312 | Cl | Cl | CH₃ | CH₃ | 4-SCH₃—Ph | |
| 3.313 | Cl | Cl | CH₃ | CH₃ | 3-OCH₃—Ph | |
| 3.314 | Cl | Cl | CH₃ | CH₃ | 3-Cl—Ph | |
| 3.315 | Cl | Cl | CH₃ | CH₃ | 3,4-Cl₂—Ph | |
| 3.316 | Cl | Cl | CH₃ | CH₃ | 3-Cl-4-F—Ph | |
| 3.317 | Cl | Cl | CH₃ | OCH₃ | 4-F—Ph | |
| 3.318 | Cl | Cl | CH₃ | OCH₃ | 4-Cl—Ph | |
| 3.319 | Cl | Cl | CH₃ | OCH₃ | 3-CF₃—Ph | |
| 3.320 | Cl | Cl | CH₃ | OCH₃ | 4-CF₃—Ph | |
| 3.321 | Cl | Cl | CH₃ | OCH₃ | 4-OCF₃—Ph | |
| 3.322 | Cl | Cl | CH₃ | OCH₃ | 4-t-Butyl-Ph | |
| 3.323 | Cl | Cl | CH₃ | OCH₃ | 2,4-Cl₂—Ph | |
| 3.324 | Cl | Cl | CH₃ | OCH₃ | 3,5-Cl₂—Ph | |
| 3.325 | Cl | Cl | CH₃ | OCH₃ | 2-CF₃—Ph | |
| 3.326 | Cl | Cl | CH₃ | OCH₃ | 4-OCH₃—Ph | |
| 3.327 | Cl | Cl | CH₃ | OCH₃ | 4-SCH₃—Ph | |
| 3.328 | Cl | Cl | CH₃ | OCH₃ | 3-OCH₃—Ph | |
| 3.329 | Cl | Cl | CH₃ | OCH₃ | 3-Cl—Ph | |
| 3.330 | Cl | Cl | CH₃ | OCH₃ | 3,4-Cl₂—Ph | |
| 3.331 | Cl | Cl | CH₃ | OCH₃ | 3-Cl-4-F—Ph | |
| 3.332 | Cl | Cl | CH₃ | CF₃ | 4-F—Ph | |
| 3.333 | Cl | Cl | CH₃ | CF₃ | 4-Cl—Ph | |
| 3.334 | Cl | Cl | CH₃ | CF₃ | 3-CF₃—Ph | |
| 3.335 | Cl | Cl | CH₃ | CF₃ | 4-CF₃—Ph | |
| 3.336 | Cl | Cl | CH₃ | CF₃ | 4-OCF₃—Ph | |
| 3.337 | Cl | Cl | CH₃ | CF₃ | 4-t-Butyl-Ph | |
| 3.338 | Cl | Cl | CH₃ | CF₃ | 2,4-Cl₂—Ph | |
| 3.339 | Cl | Cl | CH₃ | CF₃ | 3,5-Cl₂—Ph | |
| 3.340 | Cl | Cl | CH₃ | CF₃ | 2-CF₃—Ph | |
| 3.341 | Cl | Cl | CH₃ | CF₃ | 4-OCH₃—Ph | |
| 3.342 | Cl | Cl | CH₃ | CF₃ | 4-SCH₃—Ph | |
| 3.343 | Cl | Cl | CH₃ | CF₃ | 3-OCH₃—Ph | |
| 3.344 | Cl | Cl | CH₃ | CF₃ | 3-Cl—Ph | |
| 3.345 | Cl | Cl | CH₃ | CF₃ | 3,4-Cl₂—Ph | |
| 3.346 | Cl | Cl | CH₃ | CF₃ | 3-Cl-4-F—Ph | |
| 3.347 | F | F | SCH₃ | H | Br | 141–142° C. |
| 3.348 | F | F | OCH₃ | H | Br | 103–105° C. |
| 3.349 | F | F | Cl | H | Br | 146–148° C. |
| 3.350 | F | F | CN | H | Br | 148–150° C. |
| 3.351 | F | F | OH | H | Br | >250° C. |
| 3.352 | F | F | NH—CH₃ | H | Br | 181–183° C. |

TABLE 3-continued

Compounds of the formula

| No. | X₁ | X₂ | R₂₁ | Rₐ | Rc | phys. data |
|---|---|---|---|---|---|---|
| 3.353 | F | F | H | H | 4-F-Phenoxy | |
| 3.354 | F | F | H | H | 3-CF₃-Phenoxy | |
| 3.355 | F | F | H | H | 4-CF₃-Phenoxy | |
| 3.356 | F | F | H | H | 4-OCF₃-Phenoxy | |
| 3.357 | F | F | H | H | 4-t-Butyl-Phenoxy | |
| 3.358 | F | F | H | H | 3,5-Cl₂-Phenoxy | |
| 3.359 | F | F | H | H | 4-SCH₃-Phenoxy | |
| 3.360 | F | F | H | H | 3-Cl-4-F-Phenoxy | |
| 3.361 | F | F | H | H | 4-SCF₃-Phenoxy | |
| 3.362 | F | Cl | H | H | 4-F-Phenoxy | |
| 3.363 | F | Cl | H | H | 3-CF₃-Phenoxy | |
| 3.364 | F | Cl | H | H | 4-CF₃-Phenoxy | |
| 3.365 | F | Cl | H | H | 4-OCF₃-Phenoxy | |
| 3.366 | F | Cl | H | H | 4-t-Butyl-Phenoxy | |
| 3.367 | F | Cl | H | H | 3,5-Cl₂-Phenoxy | |
| 3.368 | F | Cl | H | H | 4-SCH₃-Phenoxy | |
| 3.369 | F | Cl | H | H | 3-Cl-4-F-Phenoxy | |
| 3.370 | F | Cl | H | H | 4-SCF₃-Phenoxy | |
| 3.371 | Cl | Cl | H | H | 4-F-Phenoxy | |
| 3.372 | Cl | Cl | H | H | 3-CF₃-Phenoxy | |
| 3.373 | Cl | Cl | H | H | 4-CF₃-Phenoxy | |
| 3.374 | Cl | Cl | H | H | 4-OCF₃-Phenoxy | |
| 3.375 | Cl | Cl | H | H | 4-t-Butyl-Phenoxy | |
| 3.376 | Cl | Cl | H | H | 3,5-Cl₂-Phenoxy | |
| 3.377 | Cl | Cl | H | H | 4-SCH₃-Phenoxy | |
| 3.378 | Cl | Cl | H | H | 3-Cl-4-F-Phenoxy | |
| 3.379 | Cl | Cl | H | H | 4-SCF₃-Phenoxy | |
| 3.380 | F | F | H | H | 4-F-Phenylamino | |
| 3.381 | F | F | H | H | 3-CF₃-Phenyl-amino | |
| 3.382 | F | F | H | H | 4-CF₃-Phenyl-amino | |
| 3.383 | F | F | H | H | 4-OCF₃-Phenyl-amino | |
| 3.384 | F | F | H | H | 4-t-Butyl-Phenyl-amino | |
| 3.385 | F | F | H | H | 3,5-Cl₂-Phenyl-amino | |
| 3.386 | F | F | H | H | 4-SCH₃-Phenyl-amino | |
| 3.387 | F | F | H | H | 3-Cl-4-F-Phenyl-amino | |
| 3.388 | F | F | H | H | 4-SCF₃-Phenyl-amino | |
| 3.389 | F | Cl | H | H | 4-F-Phenylamino | |
| 3.390 | F | Cl | H | H | 3-CF₃-Phenyl-amino | |
| 3.391 | F | Cl | H | H | 4-CF₃-Phenyl-amino | |
| 3.392 | F | Cl | H | H | 4-OCF₃-Phenyl-amino | |
| 3.393 | F | Cl | H | H | 4-t-Butyl-Phenyl-amino | |
| 3.394 | F | Cl | H | H | 3,5-Cl₂-Phenyl-amino | |
| 3.395 | F | Cl | H | H | 4-SCH₃-Phenyl-amino | |
| 3.396 | F | Cl | H | H | 3-Cl-4-F-Phenyl-amino | |
| 3.397 | F | Cl | H | H | 4-SCF₃-Phenyl-amino | |
| 3.398 | Cl | Cl | H | H | 4-F-Phenylamino | |
| 3.399 | Cl | Cl | H | H | 3-CF₃-Phenyl-amino | |
| 3.400 | Cl | Cl | H | H | 4-CF₃-Phenyl-amino | |
| 3.401 | Cl | Cl | H | H | 4-OCF₃-Phenyl-amino | |
| 3.402 | Cl | Cl | H | H | 4-t-Butyl-Phenyl-amino | |
| 3.403 | Cl | Cl | H | H | 3,5-Cl₂-Phenyl-amino | |
| 3.404 | Cl | Cl | H | H | 4-SCH₃-Phenyl-amino | |
| 3.405 | Cl | Cl | H | H | 3-Cl-4-F-Phenyl-amino | |
| 3.406 | Cl | Cl | H | H | 4-SCF₃-Phenyl-amino | |
| 3.407 | F | F | —OC₂H₅ | H | Br | 111–113 |
| 3.408 | F | F | —OCH₂CCH | H | Br | 140–142 |
| 3.409 | F | F | —O-i-Prop | H | Br | 130–132 |
| 3.410 | F | F | —NH-c-Prop | H | Br | 136–138 |
| 3.411 | F | F | —NHC₂H₅ | H | Br | 207–209 |
| 3.412 | F | F | —N(CH₃)₂ | H | Br | 236–238 |
| 3.413 | F | F | —SCH₃ | H | Br | 141–142 |
| 3.414 | F | F | —NHCH₂CCH | H | Br | 168–171 |
| 3.415 | F | F | —SC₂H₅ | H | Br | 138–140 |
| 3.416 | F | F | —SH | H | Br | 222–224 |

TABLE 3A

Compounds of the formula

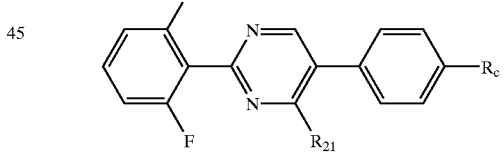

(Id)

| No. | Rc |
|---|---|
| 3A.1 | 4-F—Ph |
| 3A.2 | 4-Cl—Ph |
| 3A.3 | 3-CF₃—Ph |
| 3A.4 | 4-CF₃—Ph |
| 3A.5 | 4-OCF₃—Ph |
| 3A.6 | 4-t-Butyl-Ph |
| 3A.7 | 2,4-Cl₂—Ph |
| 3A.8 | 3,5-Cl₂—Ph |
| 3A.9 | 2-CF₃—Ph |
| 3A.10 | 4-OCH₃—Ph |
| 3A.11 | 4-SCH₃—Ph |
| 3A.12 | 3-OCH₃—Ph |
| 3A.13 | 3-Cl—Ph |
| 3A.14 | 3,4-Cl₂—Ph |
| 3A.15 | 3-Cl-4-F—Ph |
| 3A.16 | 4-Br |
| 3A.17 | 4-CH₃—Ph |

TABLE 3.1

Compounds of the general formula (Id), in which $R_{21}$ is —OH and the substituted $R_c$ for a compound in each case corresponds to a line in table 3A.

TABLE 3.2

Compounds of the general formula (Id), in which $R_{21}$ is —CN and the substituted $R_c$ for a compound in each case corresponds to a line in table 3A.

TABLE 3.3

Compounds of the general formula (Id), in which $R_{21}$ is —OCH$_3$ and the substituted $R_c$ for a compound in each case corresponds to a line in table 3A.

TABLE 3.4

Compounds of the general formula (Id), in which $R_{21}$ is —NHCH$_3$ and the substituted $R_c$ for a compound in each case corresponds to a line in table 3A.

TABLE 3.5

Compounds of the general formula (Id), in which $R_{21}$ is —SCH$_3$ and the substituted $R_c$ for a compound in each case corresponds to a line in table 3A.

TABLE 3.6

Compounds of the general formula (Id), in which $R_{21}$ is —O-i-propyl and the substituted $R_c$ for a compound in each case corresponds to a line in table 3A.

TABLE 3.7

Compounds of the general formula (Id), in which $R_{21}$ is —O—C$_2$H$_5$ and the substituted $R_c$ for a compound in each case corresponds to a line in table 3A.

TABLE 3.8

Compounds of the general formula (Id), in which $R_{21}$ is —S—C$_2$H$_5$ and the substituted $R_c$ for a compound in each case corresponds to a line in table 3A.

TABLE 3.9

Compounds of the general formula (Id), in which $R_{21}$ is —NH-c-prop and the substituted $R_c$ for a compound in each case corresponds to a line in table 3A.

TABLE 3.10

Compounds of the general formula (Id), in which $R_{21}$ is —NH—CH$_2$—CCH and the substituted $R_c$ for a compound in each case corresponds to a line in table 3A.

TABLE 3.11

Compounds of the general formula (Id), in which $R_{21}$ is —N(CH$_3$)$_2$ and the substituted $R_c$ for a compound in each case corresponds to a line in table 3A.

TABLE 3.12

Compounds of the general formula (Id), in which $R_{21}$ is —NH—C$_2$H$_5$ and the substituted $R_c$ for a compound in each case corresponds to a line in table 3A.

TABLE 3.13

Compounds of the general formula (Id), in which $R_{21}$ is —O—CH$_2$CH$_2$—OCH$_3$ and the substituted $R_c$ for a compound in each case corresponds to a line in table 3A.

TABLE 3.14

Compounds of the general formula (Id), in which $R_{21}$ is —S—CH$_2$CH$_2$—OCH$_3$ and the substituted $R_c$ for a compound in each case corresponds to a line in table 3A.

TABLE 3.15

Compounds of the general formula (Id), in which $R_{21}$ is —NH—CH$_2$CH$_2$—OCH$_3$ and the substituted $R_c$ for a compound in each case corresponds to a line in table 3A.

TABLE 4

Compounds of the formula

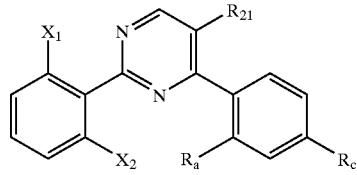

| No. | $X_1$ | $X_2$ | $R_{21}$ | $R_a$ | $R_c$ | phys. data |
|---|---|---|---|---|---|---|
| 4.1 | F | F | H | CH$_3$ | 4-F—Ph | |
| 4.2 | F | F | H | CH$_3$ | 4-Cl—Ph | |
| 4.3 | F | F | H | CH$_3$ | 3-CF$_3$—Ph | |
| 4.4 | F | F | H | CH$_3$ | 4-CF$_3$—Ph | |
| 4.5 | F | F | H | CH$_3$ | 4-OCF$_3$—Ph | |
| 4.6 | F | F | H | CH$_3$ | 4-t-Butyl-Ph | |
| 4.7 | F | F | H | CH$_3$ | 2,4-Cl$_2$—Ph | |
| 4.8 | F | F | H | CH$_3$ | 3,5-Cl$_2$—Ph | |
| 4.9 | F | F | H | CH$_3$ | 2-CF$_3$—Ph | |
| 4.10 | F | F | H | CH$_3$ | 4-OCH$_3$—Ph | |
| 4.11 | F | F | H | CH$_3$ | 4-SCH$_3$—Ph | |
| 4.12 | F | F | H | CH$_3$ | 3-OCH$_3$—Ph | |
| 4.13 | F | F | H | CH$_3$ | 3-Cl—Ph | |
| 4.14 | F | F | H | CH$_3$ | 3,4-Cl$_2$—Ph | |
| 4.15 | F | F | H | CH$_3$ | 3-Cl-4-F—Ph | |
| 4.16 | F | F | H | OCH$_3$ | 4-F—Ph | |
| 4.17 | F | F | H | OCH$_3$ | 4-Cl—Ph | |
| 4.18 | F | F | H | OCH$_3$ | 3-CF$_3$—Ph | |
| 4.19 | F | F | H | OCH$_3$ | 4-CF$_3$—Ph | |
| 4.20 | F | F | H | OCH$_3$ | 4-OCF$_3$—Ph | |
| 4.21 | F | F | H | OCH$_3$ | 4-t-Butyl-Ph | |
| 4.22 | F | F | H | OCH$_3$ | 2,4-Cl$_2$—Ph | |
| 4.23 | F | F | H | OCH$_3$ | 3,5-Cl$_2$—Ph | |
| 4.24 | F | F | H | OCH$_3$ | 2-CF$_3$—Ph | |

TABLE 4-continued

Compounds of the formula

| No. | $X_1$ | $X_2$ | $R_{21}$ | $R_a$ | $R_c$ | phys. data |
|---|---|---|---|---|---|---|
| 4.25 | F | F | H | OCH$_3$ | 4-OCH$_3$—Ph | |
| 4.26 | F | F | H | OCH$_3$ | 4-SCH$_3$—Ph | |
| 4.27 | F | F | H | OCH$_3$ | 3-OCH$_3$—Ph | |
| 4.28 | F | F | H | OCH$_3$ | 3-Cl—Ph | |
| 4.29 | F | F | H | OCH$_3$ | 3,4-Cl$_2$—Ph | |
| 4.30 | F | F | H | OCH$_3$ | 3-Cl-4-F—Ph | |
| 4.31 | F | F | H | OCH$_3$ | 4-Br | |
| 4.32 | F | F | H | CF$_3$ | 4-F—Ph | |
| 4.33 | F | F | H | CF$_3$ | 4-Cl—Ph | |
| 4.34 | F | F | H | CF$_3$ | 3-CF$_3$—Ph | |
| 4.35 | F | F | H | CF$_3$ | 4-CF$_3$—Ph | |
| 4.36 | F | F | H | CF$_3$ | 4-OCF$_3$—Ph | |
| 4.37 | F | F | H | CF$_3$ | 4-t-Butyl-Ph | |
| 4.38 | F | F | H | CF$_3$ | 2,4-Cl$_2$—Ph | |
| 4.39 | F | F | H | CF$_3$ | 3,5-Cl$_2$—Ph | |
| 4.40 | F | F | H | CF$_3$ | 2-CF$_3$—Ph | |
| 4.41 | F | F | H | CF$_3$ | 4-OCH$_3$—Ph | |
| 4.42 | F | F | H | CF$_3$ | 4-SCH$_3$—Ph | |
| 4.43 | F | F | H | CF$_3$ | 3-OCH$_3$—Ph | |
| 4.44 | F | F | H | CF$_3$ | 3-Cl—Ph | |
| 4.45 | F | F | H | CF$_3$ | 3,4-Cl$_2$—Ph | |
| 4.46 | F | F | H | CF$_3$ | 3-Cl-4-F—Ph | |
| 4.47 | F | F | CH$_3$ | H | 4-F—Ph | |
| 4.48 | F | F | CH$_3$ | H | 4-Cl—Ph | |
| 4.49 | F | F | CH$_3$ | H | 3-CF$_3$—Ph | |
| 4.50 | F | F | CH$_3$ | H | 4-CF$_3$—Ph | |
| 4.51 | F | F | CH$_3$ | H | 4-OCF$_3$—Ph | |
| 4.52 | F | F | CH$_3$ | H | 4-t-Butyl-Ph | |
| 4.53 | F | F | CH$_3$ | H | 2,4-Cl$_2$—Ph | |
| 4.54 | F | F | CH$_3$ | H | 3,5-Cl$_2$—Ph | |
| 4.55 | F | F | CH$_3$ | H | 2-CF$_3$—Ph | |
| 4.56 | F | F | CH$_3$ | H | 4-OCH$_3$—Ph | |
| 4.57 | F | F | CH$_3$ | H | 4-SCH$_3$—Ph | |
| 4.58 | F | F | CH$_3$ | H | 3-OCH$_3$—Ph | |
| 4.59 | F | F | CH$_3$ | H | 3-Cl—Ph | |
| 4.60 | F | F | CH$_3$ | H | 3,4-Cl$_2$—Ph | |
| 4.61 | F | F | CH$_3$ | H | 3-Cl-4-F—Ph | |
| 4.62 | F | F | CH$_3$ | CH$_3$ | 4-F—Ph | |
| 4.63 | F | F | CH$_3$ | CH$_3$ | 4-Cl—Ph | |
| 4.64 | F | F | CH$_3$ | CH$_3$ | 3-CF$_3$—Ph | |
| 4.65 | F | F | CH$_3$ | CH$_3$ | 4-CF$_3$—Ph | |
| 4.66 | F | F | CH$_3$ | CH$_3$ | 4-OCF$_3$—Ph | |
| 4.67 | F | F | CH$_3$ | CH$_3$ | 4-t-Butyl-Ph | |
| 4.68 | F | F | CH$_3$ | CH$_3$ | 2,4-Cl$_2$—Ph | |
| 4.69 | F | F | CH$_3$ | CH$_3$ | 3,5-Cl$_2$—Ph | |
| 4.70 | F | F | CH$_3$ | CH$_3$ | 2-CF$_3$—Ph | |
| 4.71 | F | F | CH$_3$ | CH$_3$ | 4-OCH$_3$—Ph | |
| 4.72 | F | F | CH$_3$ | CH$_3$ | 4-SCH$_3$—Ph | |
| 4.73 | F | F | CH$_3$ | CH$_3$ | 3-OCH$_3$—Ph | |
| 4.74 | F | F | CH$_3$ | CH$_3$ | 3-Cl—Ph | |
| 4.75 | F | F | CH$_3$ | CH$_3$ | 3,4-Cl$_2$—Ph | |
| 4.76 | F | F | CH$_3$ | CH$_3$ | 3-Cl-4-F—Ph | |
| 4.77 | F | F | CH$_3$ | OCH$_3$ | 4-F—Ph | |
| 4.78 | F | F | CH$_3$ | OCH$_3$ | 4-Cl—Ph | |
| 4.79 | F | F | CH$_3$ | OCH$_3$ | 3-CF$_3$—Ph | |
| 4.80 | F | F | CH$_3$ | OCH$_3$ | 4-CF$_3$—Ph | |
| 4.81 | F | F | CH$_3$ | OCH$_3$ | 4-OCF$_3$—Ph | |
| 4.82 | F | F | CH$_3$ | OCH$_3$ | 4-t-Butyl-Ph | |
| 4.83 | F | F | CH$_3$ | OCH$_3$ | 2,4-Cl$_2$—Ph | |
| 4.84 | F | F | CH$_3$ | OCH$_3$ | 3,5-Cl$_2$—Ph | |
| 4.85 | F | F | CH$_3$ | OCH$_3$ | 2-CF$_3$—Ph | |
| 4.86 | F | F | CH$_3$ | OCH$_3$ | 4-OCH$_3$—Ph | |
| 4.87 | F | F | CH$_3$ | OCH$_3$ | 4-SCH$_3$—Ph | |
| 4.88 | F | F | CH$_3$ | OCH$_3$ | 3-OCH$_3$—Ph | |
| 4.89 | F | F | CH$_3$ | OCH$_3$ | 3-Cl—Ph | |
| 4.90 | F | F | CH$_3$ | OCH$_3$ | 3,4-Cl$_2$—Ph | |
| 4.91 | F | F | CH$_3$ | OCH$_3$ | 3-Cl-4-F—Ph | |
| 4.92 | F | F | CH$_3$ | CF$_3$ | 4-F—Ph | |
| 4.93 | F | F | CH$_3$ | CF$_3$ | 4-Cl—Ph | |
| 4.94 | F | F | CH$_3$ | CF$_3$ | 3-CF$_3$—Ph | |
| 4.95 | F | F | CH$_3$ | CF$_3$ | 4-CF$_3$—Ph | |
| 4.96 | F | F | CH$_3$ | CF$_3$ | 4-OCF$_3$—Ph | |
| 4.97 | F | F | CH$_3$ | CF$_3$ | 4-t-Butyl-Ph | |
| 4.98 | F | F | CH$_3$ | CF$_3$ | 2,4-Cl$_2$—Ph | |
| 4.99 | F | F | CH$_3$ | CF$_3$ | 3,5-Cl$_2$—Ph | |
| 4.100 | F | F | CH$_3$ | CF$_3$ | 2-CF$_3$—Ph | |
| 4.101 | F | F | CH$_3$ | CF$_3$ | 4-OCH$_3$—Ph | |
| 4.102 | F | F | CH$_3$ | CF$_3$ | 4-SCH$_3$—Ph | |
| 4.103 | F | F | CH$_3$ | CF$_3$ | 3-OCH$_3$—Ph | |
| 4.104 | F | F | CH$_3$ | CF$_3$ | 3-Cl—Ph | |
| 4.105 | F | F | CH$_3$ | CF$_3$ | 3,4-Cl$_2$—Ph | |
| 4.106 | F | F | CH$_3$ | CF$_3$ | 3-Cl-4-F—Ph | |
| 4.107 | F | Cl | H | H | 4-F—Ph | |
| 4.108 | F | Cl | H | H | 4-Cl—Ph | |
| 4.109 | F | Cl | H | H | 3-CF$_3$—Ph | |
| 4.110 | F | Cl | H | H | 4-CF$_3$—Ph | |
| 4.111 | F | Cl | H | H | 4-OCF$_3$—Ph | |
| 4.112 | F | Cl | H | H | 4-t-Butyl-Ph | |
| 4.113 | F | Cl | H | H | 2,4-Cl$_2$—Ph | |
| 4.114 | F | Cl | H | H | 3,5-Cl$_2$—Ph | |
| 4.115 | F | Cl | H | H | 2-CF$_3$—Ph | |
| 4.116 | F | Cl | H | H | 4-OCH$_3$—Ph | |
| 4.117 | F | Cl | H | H | 4-SCH$_3$—Ph | |
| 4.118 | F | Cl | H | H | 3-OCH$_3$—Ph | |
| 4.119 | F | Cl | H | H | 3-Cl—Ph | |
| 4.120 | F | Cl | H | H | 3,4-Cl$_2$—Ph | |
| 4.121 | F | Cl | H | H | 3-Cl-4-F—Ph | |
| 4.122 | F | Cl | H | CH$_3$ | 4-F—Ph | |
| 4.123 | F | Cl | H | CH$_3$ | 4-Cl—Ph | |
| 4.124 | F | Cl | H | CH$_3$ | 3-CF$_3$—Ph | |
| 4.125 | F | Cl | H | CH$_3$ | 4-CF$_3$—Ph | |
| 4.126 | F | Cl | H | CH$_3$ | 4-OCF$_3$—Ph | |
| 4.127 | F | Cl | H | CH$_3$ | 4-t-Butyl-Ph | |
| 4.128 | F | Cl | H | CH$_3$ | 2,4-Cl$_2$—Ph | |
| 4.129 | F | Cl | H | CH$_3$ | 3,5-Cl$_2$—Ph | |
| 4.130 | F | Cl | H | CH$_3$ | 2-CF$_3$—Ph | |
| 4.131 | F | Cl | H | CH$_3$ | 4-OCH$_3$—Ph | |
| 4.132 | F | Cl | H | CH$_3$ | 4-SCH$_3$—Ph | |
| 4.133 | F | Cl | H | CH$_3$ | 3-OCH$_3$—Ph | |
| 4.134 | F | Cl | H | CH$_3$ | 3-Cl—Ph | |
| 4.135 | F | Cl | H | CH$_3$ | 3,4-Cl$_2$—Ph | |
| 4.136 | F | Cl | H | CH$_3$ | 3-Cl-4-F—Ph | |
| 4.137 | F | Cl | H | OCH$_3$ | 4-F—Ph | |
| 4.138 | F | Cl | H | OCH$_3$ | 4-Cl—Ph | |
| 4.139 | F | Cl | H | OCH$_3$ | 3-CF$_3$—Ph | |
| 4.140 | F | Cl | H | OCH$_3$ | 4-CF$_3$—Ph | |
| 4.141 | F | Cl | H | OCH$_3$ | 4-OCF$_3$—Ph | |
| 4.142 | F | Cl | H | OCH$_3$ | 4-t-Butyl-Ph | |
| 4.143 | F | Cl | H | OCH$_3$ | 2,4-Cl$_2$—Ph | |
| 4.144 | F | Cl | H | OCH$_3$ | 3,5-Cl$_2$—Ph | |
| 4.145 | F | Cl | H | OCH$_3$ | 2-CF$_3$—Ph | |
| 4.146 | F | Cl | H | OCH$_3$ | 4-OCH$_3$—Ph | |
| 4.147 | F | Cl | H | OCH$_3$ | 4-SCH$_3$—Ph | |
| 4.148 | F | Cl | H | OCH$_3$ | 3-OCH$_3$—Ph | |
| 4.149 | F | Cl | H | OCH$_3$ | 3-Cl—Ph | |
| 4.150 | F | Cl | H | OCH$_3$ | 3,4-Cl$_2$—Ph | |
| 4.151 | F | Cl | H | OCH$_3$ | 3-Cl-4-F—Ph | |
| 4.152 | F | Cl | H | CF$_3$ | 4-F—Ph | |
| 4.153 | F | Cl | H | CF$_3$ | 4-Cl—Ph | |
| 4.154 | F | Cl | H | CF$_3$ | 3-CF$_3$—Ph | |

TABLE 4-continued

Compounds of the formula

| No. | X₁ | X₂ | R₂₁ | Rₐ | R_c | phys. data |
|---|---|---|---|---|---|---|
| 4.155 | F | Cl | H | CF₃ | 4-CF₃—Ph | |
| 4.156 | F | Cl | H | CF₃ | 4-OCF₃—Ph | |
| 4.157 | F | Cl | H | CF₃ | 4-t-Butyl-Ph | |
| 4.158 | F | Cl | H | CF₃ | 2,4-Cl₂—Ph | |
| 4.159 | F | Cl | H | CF₃ | 3,5-Cl₂—Ph | |
| 4.160 | F | Cl | H | CF₃ | 2-CF₃—Ph | |
| 4.161 | F | Cl | H | CF₃ | 4-OCH₃—Ph | |
| 4.162 | F | Cl | H | CF₃ | 4-SCH₃—Ph | |
| 4.163 | F | Cl | H | CF₃ | 3-OCH₃—Ph | |
| 4.164 | F | Cl | H | CF₃ | 3-Cl—Ph | |
| 4.165 | F | Cl | H | CF₃ | 3,4-Cl₂—Ph | |
| 4.166 | F | Cl | H | CF₃ | 3-Cl-4-F—Ph | |
| 4.167 | F | Cl | CH₃ | H | 4-F—Ph | |
| 4.168 | F | Cl | CH₃ | H | 4-Cl—Ph | |
| 4.169 | F | Cl | CH₃ | H | 3-CF₃—Ph | |
| 4.170 | F | Cl | CH₃ | H | 4-CF₃—Ph | |
| 4.171 | F | Cl | CH₃ | H | 4-OCF₃—Ph | |
| 4.172 | F | Cl | CH₃ | H | 4-t-Butyl-Ph | |
| 4.173 | F | Cl | CH₃ | H | 2,4-Cl₂—Ph | |
| 4.174 | F | Cl | CH₃ | H | 3,5-Cl₂—Ph | |
| 4.175 | F | Cl | CH₃ | H | 2-CF₃—Ph | |
| 4.176 | F | Cl | CH₃ | H | 4-OCH₃—Ph | |
| 4.177 | F | Cl | CH₃ | H | 4-SCH₃—Ph | |
| 4.178 | F | Cl | CH₃ | H | 3-OCH₃—Ph | |
| 4.179 | F | Cl | CH₃ | H | 3-Cl—Ph | |
| 4.180 | F | Cl | CH₃ | H | 3,4-Cl₂—Ph | |
| 4.181 | F | Cl | CH₃ | H | 3-Cl-4-F—Ph | |
| 4.182 | F | Cl | CH₃ | CH₃ | 4-F—Ph | |
| 4.183 | F | Cl | CH₃ | CH₃ | 4-Cl—Ph | |
| 4.184 | F | Cl | CH₃ | CH₃ | 3-CF₃—Ph | |
| 4.185 | F | Cl | CH₃ | CH₃ | 4-CF₃—Ph | |
| 4.186 | F | Cl | CH₃ | CH₃ | 4-OCH₃—Ph | |
| 4.187 | F | Cl | CH₃ | CH₃ | 4-t-Butyl-Ph | |
| 4.188 | F | Cl | CH₃ | CH₃ | 2,4-Cl₂—Ph | |
| 4.189 | F | Cl | CH₃ | CH₃ | 3,5-Cl₂—Ph | |
| 4.190 | F | Cl | CH₃ | CH₃ | 2-CF₃—Ph | |
| 4.191 | F | Cl | CH₃ | CH₃ | 4-OCH₃—Ph | |
| 4.192 | F | Cl | CH₃ | CH₃ | 4-SCH₃—Ph | |
| 4.193 | F | Cl | CH₃ | CH₃ | 3-OCH₃—Ph | |
| 4.194 | F | Cl | CH₃ | CH₃ | 3-Cl—Ph | |
| 4.195 | F | Cl | CH₃ | CH₃ | 3,4-Cl₂—Ph | |
| 4.196 | F | Cl | CH₃ | CH₃ | 3-Cl-4-F—Ph | |
| 4.197 | F | Cl | CH₃ | OCH₃ | 4-F—Ph | |
| 4.198 | F | Cl | CH₃ | OCH₃ | 4-Cl—Ph | |
| 4.199 | F | Cl | CH₃ | OCH₃ | 3-CF₃—Ph | |
| 4.200 | F | Cl | CH₃ | OCH₃ | 4-CF₃—Ph | |
| 4.201 | F | Cl | CH₃ | OCH₃ | 4-OCF₃—Ph | |
| 4.202 | F | Cl | CH₃ | OCH₃ | 4-t-Butyl-Ph | |
| 4.203 | F | Cl | CH₃ | OCH₃ | 2,4-Cl₂—Ph | |
| 4.204 | F | Cl | CH₃ | OCH₃ | 3,5-Cl₂—Ph | |
| 4.205 | F | Cl | CH₃ | OCH₃ | 2-CF₃—Ph | |
| 4.206 | F | Cl | CH₃ | OCH₃ | 4-OCH₃—Ph | |
| 4.207 | F | Cl | CH₃ | OCH₃ | 4-SCH₃—Ph | |
| 4.208 | F | Cl | CH₃ | OCH₃ | 3-OCH₃—Ph | |
| 4.209 | F | Cl | CH₃ | OCH₃ | 3-Cl—Ph | |
| 4.210 | F | Cl | CH₃ | OCH₃ | 3,4-Cl₂—Ph | |
| 4.211 | F | Cl | CH₃ | OCH₃ | 3-Cl-4-F—Ph | |
| 4.212 | F | Cl | CH₃ | CF₃ | 4-F—Ph | |
| 4.213 | F | Cl | CH₃ | CF₃ | 4-Cl—Ph | |
| 4.214 | F | Cl | CH₃ | CF₃ | 3-CF₃—Ph | |
| 4.215 | F | Cl | CH₃ | CF₃ | 4-CF₃—Ph | |
| 4.216 | F | Cl | CH₃ | CF₃ | 4-OCF₃—Ph | |
| 4.217 | F | Cl | CH₃ | CF₃ | 4-t-Butyl-Ph | |
| 4.218 | F | Cl | CH₃ | CF₃ | 2,4-Cl₂—Ph | |
| 4.219 | F | Cl | CH₃ | CF₃ | 3,5-Cl₂—Ph | |
| 4.220 | F | Cl | CH₃ | CF₃ | 2-CF₃—Ph | |
| 4.221 | F | Cl | CH₃ | CF₃ | 4-OCH₃—Ph | |
| 4.222 | F | Cl | CH₃ | CF₃ | 4-SCH₃—Ph | |
| 4.223 | F | Cl | CH₃ | CF₃ | 3-OCH₃—Ph | |
| 4.224 | F | Cl | CH₃ | CF₃ | 3-Cl—Ph | |
| 4.225 | F | Cl | CH₃ | CF₃ | 3,4-Cl₂—Ph | |
| 4.226 | F | Cl | CH₃ | CF₃ | 3-Cl-4-F—Ph | |
| 4.227 | Cl | Cl | H | H | 4-F—Ph | |
| 4.228 | Cl | Cl | H | H | 4-Cl—Ph | |
| 4.229 | Cl | Cl | H | H | 3-CF₃—Ph | |
| 4.230 | Cl | Cl | H | H | 4-CF₃—Ph | |
| 4.231 | Cl | Cl | H | H | 4-OCF₃—Ph | |
| 4.232 | Cl | Cl | H | H | 4-t-Butyl-Ph | |
| 4.233 | Cl | Cl | H | H | 2,4-Cl₂—Ph | |
| 4.234 | Cl | Cl | H | H | 3,5-Cl₂—Ph | |
| 4.235 | Cl | Cl | H | H | 2-CF₃—Ph | |
| 4.236 | Cl | Cl | H | H | 4-OCH₃—Ph | |
| 4.237 | Cl | Cl | H | H | 4-SCH₃—Ph | |
| 4.238 | Cl | Cl | H | H | 3-OCH₃—Ph | |
| 4.239 | Cl | Cl | H | H | 3-Cl—Ph | |
| 4.240 | Cl | Cl | H | H | 3,4-Cl₂—Ph | |
| 4.241 | Cl | Cl | H | H | 3-Cl-4-F—Ph | |
| 4.242 | Cl | Cl | H | CH₃ | 4-F—Ph | |
| 4.243 | Cl | Cl | H | CH₃ | 4-Cl—Ph | |
| 4.244 | Cl | Cl | H | CH₃ | 3-CF₃—Ph | |
| 4.245 | Cl | Cl | H | CH₃ | 4-CF₃—Ph | |
| 4.246 | Cl | Cl | H | CH₃ | 4-CF₃—Ph | |
| 4.247 | Cl | Cl | H | CH₃ | 4-t-Butyl-Ph | |
| 4.248 | Cl | Cl | H | CH₃ | 2,4-Cl₂—Ph | |
| 4.249 | Cl | Cl | H | CH₃ | 3,5-Cl₂—Ph | |
| 4.250 | Cl | Cl | H | CH₃ | 2-CF₃—Ph | |
| 4.251 | Cl | Cl | H | CH₃ | 4-OCH₃—Ph | |
| 4.252 | Cl | Cl | H | CH₃ | 4-SCH₃—Ph | |
| 4.253 | Cl | Cl | H | CH₃ | 3-OCH₃—Ph | |
| 4.254 | Cl | Cl | H | CH₃ | 3-Cl—Ph | |
| 4.255 | Cl | Cl | H | CH₃ | 3,4-Cl₂—Ph | |
| 4.256 | Cl | Cl | H | CH₃ | 3-Cl-4-F—Ph | |
| 4.257 | Cl | Cl | H | OCH₃ | 4-F—Ph | |
| 4.258 | Cl | Cl | H | OCH₃ | 4-Cl—Ph | |
| 4.259 | Cl | Cl | H | OCH₃ | 3-CF₃—Ph | |
| 4.260 | Cl | Cl | H | OCH₃ | 4-CF₃—Ph | |
| 4.261 | Cl | Cl | H | OCH₃ | 4-OCF₃—Ph | |
| 4.262 | Cl | Cl | H | OCH₃ | 4-t-Butyl-Ph | |
| 4.263 | Cl | Cl | H | OCH₃ | 2,4-Cl₂—Ph | |
| 4.264 | Cl | Cl | H | OCH₃ | 3,5-Cl₂—Ph | |
| 4.265 | Cl | Cl | H | OCH₃ | 2-CF₃—Ph | |
| 4.266 | Cl | Cl | H | OCH₃ | 4-OCH₃—Ph | |
| 4.267 | Cl | Cl | H | OCH₃ | 4-SCH₃—Ph | |
| 4.268 | Cl | Cl | H | OCH₃ | 3-OCH₃—Ph | |
| 4.269 | Cl | Cl | H | OCH₃ | 3-Cl—Ph | |
| 4.270 | Cl | Cl | H | OCH₃ | 3,4-Cl₂—Ph | |
| 4.271 | Cl | Cl | H | OCH₃ | 3-Cl-4-F—Ph | |
| 4.272 | Cl | Cl | H | CF₃ | 4-F—Ph | |
| 4.273 | Cl | Cl | H | CF₃ | 4-Cl—Ph | |
| 4.274 | Cl | Cl | H | CF₃ | 3-CF₃—Ph | |
| 4.275 | Cl | Cl | H | CF₃ | 4-CF₃—Ph | |
| 4.276 | Cl | Cl | H | CF₃ | 4-OCF₃—Ph | |
| 4.277 | Cl | Cl | H | CF₃ | 4-t-Butyl-Ph | |
| 4.278 | Cl | Cl | H | CF₃ | 2,4-Cl₂—Ph | |
| 4.279 | Cl | Cl | H | CF₃ | 3,5-Cl₂—Ph | |
| 4.280 | Cl | Cl | H | CF₃ | 2Ph | |
| 4.281 | Cl | Cl | H | CF₃ | 4-OCH₃—Ph | |
| 4.282 | Cl | Cl | H | CF₃ | 4-SCH₃—Ph | |
| 4.283 | Cl | Cl | H | CF₃ | 3-OCH₃—Ph | |
| 4.284 | Cl | Cl | H | CF₃ | 3-Cl—Ph | |

TABLE 4-continued

Compounds of the formula

| No. | $X_1$ | $X_2$ | $R_{21}$ | $R_a$ | $R_c$ | phys. data |
|---|---|---|---|---|---|---|
| 4.285 | Cl | Cl | H | $CF_3$ | 3,4-$Cl_2$—Ph | |
| 4.286 | Cl | Cl | H | $CF_3$ | 3-Cl-4-F—Ph | |
| 4.287 | Cl | Cl | $CH_3$ | H | 4-F—Ph | |
| 4.288 | Cl | Cl | $CH_3$ | H | 4-Cl—Ph | |
| 4.289 | Cl | Cl | $CH_3$ | H | 3-$CF_3$—Ph | |
| 4.290 | Cl | Cl | $CH_3$ | H | 4-$CF_3$—Ph | |
| 4.291 | Cl | Cl | $CH_3$ | H | 4-$OCF_3$—Ph | |
| 4.292 | Cl | Cl | $CH_3$ | H | 4-t-Butyl-Ph | |
| 4.293 | Cl | Cl | $CH_3$ | H | 2,4-$Cl_2$—Ph | |
| 4.294 | Cl | Cl | $CH_3$ | H | 3,5-$Cl_2$—Ph | |
| 4.295 | Cl | Cl | $CH_3$ | H | 2-$CF_3$—Ph | |
| 4.296 | Cl | Cl | $CH_3$ | H | 4-$OCH_3$—Ph | |
| 4.297 | Cl | Cl | $CH_3$ | H | 4-$SCH_3$—Ph | |
| 4.298 | Cl | Cl | $CH_3$ | H | 3-$OCH_3$—Ph | |
| 4.299 | Cl | Cl | $CH_3$ | H | 3-Cl—Ph | |
| 4.300 | Cl | Cl | $CH_3$ | H | 3,4-$Cl_2$—Ph | |
| 4.301 | Cl | Cl | $CH_3$ | H | 3-Cl-4-F—Ph | |
| 4.302 | Cl | Cl | $CH_3$ | $CH_3$ | 4-F—Ph | |
| 4.303 | Cl | Cl | $CH_3$ | $CH_3$ | 4-Cl—Ph | |
| 4.304 | Cl | Cl | $CH_3$ | $CH_3$ | 3-$CF_3$—Ph | |
| 4.305 | Cl | Cl | $CH_3$ | $CH_3$ | 4-$CF_3$—Ph | |
| 4.306 | Cl | Cl | $CH_3$ | $CH_3$ | 4-$OCF_3$—Ph | |
| 4.307 | Cl | Cl | $CH_3$ | $CH_3$ | 4-t-Butyl-Ph | |
| 4.308 | Cl | Cl | $CH_3$ | $CH_3$ | 2,4-$Cl_2$—Ph | |
| 4.309 | Cl | Cl | $CH_3$ | $CH_3$ | 3,5-$Cl_2$—Ph | |
| 4.310 | Cl | Cl | $CH_3$ | $CH_3$ | 2-$CF_3$—Ph | |
| 4.311 | Cl | Cl | $CH_3$ | $CH_3$ | 4-$OCH_3$—Ph | |
| 4.312 | Cl | Cl | $CH_3$ | $CH_3$ | 4-$SCH_3$—Ph | |
| 4.313 | Cl | Cl | $CH_3$ | $CH_3$ | 3-$OCH_3$—Ph | |
| 4.314 | Cl | Cl | $CH_3$ | $CH_3$ | 3-Cl—Ph | |
| 4.315 | Cl | Cl | $CH_3$ | $CH_3$ | 3,4-$Cl_2$—Ph | |
| 4.316 | Cl | Cl | $CH_3$ | $CH_3$ | 3-Cl-4-F—Ph | |
| 4.317 | Cl | Cl | $CH_3$ | $OCH_3$ | 4-F—Ph | |
| 4.318 | Cl | Cl | $CH_3$ | $OCH_3$ | 4-Cl—Ph | |
| 4.319 | Cl | Cl | $CH_3$ | $OCH_3$ | 3-$CF_3$—Ph | |
| 4.320 | Cl | Cl | $CH_3$ | $OCH_3$ | 4-$CF_3$—Ph | |
| 4.321 | Cl | Cl | $CH_3$ | $OCH_3$ | 4-$OCF_3$—Ph | |
| 4.322 | Cl | Cl | $CH_3$ | $OCH_3$ | 4-t-Butyl-Ph | |
| 4.323 | Cl | Cl | $CH_3$ | $OCH_3$ | 2,4-$Cl_2$—Ph | |
| 4.324 | Cl | Cl | $CH_3$ | $OCH_3$ | 3,5-$Cl_2$—Ph | |
| 4.325 | Cl | Cl | $CH_3$ | $OCH_3$ | 2-$CF_3$—Ph | |
| 4.326 | Cl | Cl | $CH_3$ | $OCH_3$ | 4-$OCH_3$—Ph | |
| 4.327 | Cl | Cl | $CH_3$ | $OCH_3$ | 4-$SCH_3$—Ph | |
| 4.328 | Cl | Cl | $CH_3$ | $OCH_3$ | 3-$OCH_3$—Ph | |
| 4.329 | Cl | Cl | $CH_3$ | $OCH_3$ | 3-Cl—Ph | |
| 4.330 | Cl | Cl | $CH_3$ | $OCH_3$ | 3,4-$Cl_2$—Ph | |
| 4.331 | Cl | Cl | $CH_3$ | $OCH_3$ | 3-Cl-4-F—Ph | |
| 4.332 | Cl | Cl | $CH_3$ | $CF_3$ | 4-F—Ph | |
| 4.333 | Cl | Cl | $CH_3$ | $CF_3$ | 4-Cl—Ph | |
| 4.334 | Cl | Cl | $CH_3$ | $CF_3$ | 3-$CF_3$—Ph | |
| 4.335 | Cl | Cl | $CH_3$ | $CF_3$ | 4-$CF_3$—Ph | |
| 4.336 | Cl | Cl | $CH_3$ | $CF_3$ | 4-$OCF_3$—Ph | |
| 4.337 | Cl | Cl | $CH_3$ | $CF_3$ | 4-t-Butyl-Ph | |
| 4.338 | Cl | Cl | $CH_3$ | $CF_3$ | 2,4-$Cl_2$—Ph | |
| 4.339 | Cl | Cl | $CH_3$ | $CF_3$ | 3,5-$Cl_2$—Ph | |
| 4.340 | Cl | Cl | $CH_3$ | $CF_3$ | 2-$CF_3$—Ph | |
| 4.341 | Cl | Cl | $CH_3$ | $CF_3$ | 4-$OCH_3$—Ph | |
| 4.342 | Cl | Cl | $CH_3$ | $CF_3$ | 4-$SCH_3$—Ph | |
| 4.343 | Cl | Cl | $CH_3$ | $CF_3$ | 3-$OCH_3$—Ph | |
| 4.344 | Cl | Cl | $CH_3$ | $CF_3$ | 3-Cl—Ph | |
| 4.345 | Cl | Cl | $CH_3$ | $CF_3$ | 3,4-$Cl_2$—Ph | |
| 4.346 | Cl | Cl | $CH_3$ | $CF_3$ | 3-Cl-4-F—Ph | |

TABLE 5

Compounds of the formula

| No. | $X_1$ | $X_2$ | $R_{21}$ | $R_{22}$ | $R_a$ | phys. data |
|---|---|---|---|---|---|---|
| 5.1 | F | F | OH | OH | 4-Br | >300 |
| 5.2 | F | F | OH | H | 3-Br | 220–222 |
| 5.3 | F | F | Cl | Cl | 4-Br | 221–222 |
| 5.4 | F | F | Cl | H | 3-Br | 88–90 |
| 5.5 | F | F | $OCH_3$ | H | 3-Br | 89–91 |
| 5.6 | F | F | CN | H | 3-Br | 185–187 |
| 5.7 | F | F | Cl | $OCH_3$ | 4-Br | 169–171 |
| 5.8 | F | F | $OCH_3$ | H | 3-(4-$OCF_3$—Ph) | 120–122 |
| 5.9 | F | F | $OCH_3$ | H | 3-(4-$CF_3$—Ph) | 154–156 |
| 5.10 | F | F | $OCH_3$ | H | 3-(3,5-$Cl_2$—Ph) | 143–145 |
| 5.11 | F | F | CN | H | 3-(4-$OCF_3$—Ph) | 91–93 |
| 5.12 | F | F | CN | H | 3-(4-$CF_3$—PH) | 114–117 |
| 5.1 | F | F | OH | OH | 4-Br | >300 |
| 5.2 | F | F | OH | H | 3-Br | 220–222 |
| 5.3 | F | F | Cl | Cl | 4-Br | 221–222 |
| 5.4 | F | F | Cl | H | 3-Br | 88–90 |
| 5.5 | F | F | $OCH_3$ | H | 3-Br | 89–91 |
| 5.6 | F | F | CN | H | 3-Br | 185–187 |
| 5.7 | F | F | Cl | $OCH_3$ | 4-Br | 169–171 |
| 5.13 | F | F | CN | H | 3-(3,5-$Cl_2$—Ph) | 161–163 |

2. FORMULATION EXAMPLES

| 2.1. Emulsion concentrates | a) | b) | c) |
|---|---|---|---|
| active ingredient | 25% | 40% | 50% |
| calcium dodecylbenzenesulfonate | 5% | 8% | 6% |
| ricinus polyethylene glycol ether (36 mols ethylene oxide) | 5% | — | — |
| tributylphenol polyethylene glycol ether (30 mols ethylene oxide) | — | 12% | 4% |
| cyclohexanone | — | 15% | 20% |
| xylene mixture | 65% | 25% | 20% |

Emulsions of any desired concentration can be prepared from these concentrates by dilution with water.

| 2.2. Emulsion concentrates | a) | b) | c) |
|---|---|---|---|
| active ingredient | 10% | 8% | 60% |
| octylphenol polyethylene glycol ether (4–5 mols ethylene oxide) | 3% | 3% | 2% |
| calcium dodecylbenzene sulfonate | 3% | 4% | 4% |
| ricinus polyethylene glycol ether (35 mols ethylene oxide) | 4% | 5% | 4% |
| cyclohexanone | 30% | 40% | 15% |
| xylene mixture | 50% | 40% | 15% |

Emulsions of any desired concentration can be prepared from these concentrates by dilution with water.

| 2.3. Suspension concentrate | |
|---|---|
| active ingredient | 40% |
| ethylene glycol | 10% |
| nonylphenol polyethylene glycol ether (15 mols ethylene oxide) | 6% |
| sodium ligninsulfonate | 10% |
| carboxymethylcellulose | 1% |
| 37% aqueous formaldehyde solution | 0.2% |
| silicone oil in the form of a 75% aqueous | 0.8% |

| -continued | | | |
|---|---|---|---|
| emulsion | | | |
| water | 32% | | |

The finely ground active substance is intimately mixed with the adjuvants. In this way, a suspension concentrate is obtained from which suspensions of any desired concentration can be prepared by dilution with water.

| 2.4. Powder mixtures that are dispersible in water | a) | b) | c) |
|---|---|---|---|
| active ingredient | 25% | 50% | 75% |
| sodium ligninsulfonate | 5% | 5% | — |
| oleic acid | 3% | — | 5% |
| sodium diisobutylnaphthalene sulfonate | — | 6% | 10% |
| octylphenol polyethylene glycol ether (7–8 mols ethylene oxide) | — | 2% | — |
| highly dispersed silicic acid | 5% | 10% | 10% |
| kaolin | 62% | 27% | — |

The active ingredient is thoroughly mixed with the adjuvants and this mixture is ground in a suitable mill to give wettable powders which can be diluted with water to give suspensions of any desired concentration.

| 2.5. Dusts | a) | b) |
|---|---|---|
| active ingredient from tables 1 to 6 | 2% | 5% |
| highly dispersed silicic acid | 1% | 5% |
| talc | 97% | — |
| kaolin | — | 90% |

Ready-to-use dusts are obtained by intimately mixing the carriers with the active ingredients and grinding the mixture.

| 2.6. Granulate | a) | b) |
|---|---|---|
| active ingredient from tables 1 to 6 | 5% | 10% |
| kaolin | 94% | — |
| highly dispersed silicic acid | 1% | — |
| attapulgite | — | 90% |

The active ingredient is dissolved in methylene chloride, the solution is sprayed on to the carrier, and the solvent is then evaporated under vacuum. Granulates of this kind can be mixed with the animal feed.

| 2.7. Granulate | |
|---|---|
| active ingredient | 10% |
| sodium ligninsulfonate | 2% |
| carboxymethylcellulose | 1% |
| kaolin | 87% |

The active ingredient is mixed and ground with the adjuvants, and the mixture is moistened with water. This mixture is extruded and then dried in a stream of air.

| 2.8. Granulate | |
|---|---|
| active ingredient | 3% |
| Polyethylene glycol (MW 200) | 3% |
| kaolin | 94% |

(MW = molecular weight)
The finely ground active substance is uniformly applied in a mixer to the kaolin moistened with polyethylene glycol. Non-dusty coated granulates are obtained in this manner.

| 2.9 Tablets Composition (for 1000 tablets) | |
|---|---|
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

All solid ingredients are first passed through a sieve with a mesh size of 0.6 mm. The active ingredient, the lactose, the talc, and half the starch are then mixed. The other half of the starch is suspended in 40 ml water, and this suspension is added to a boiling solution of the polyethylene glycol in 100 ml water. The resulting starch paste is added to the mixture, and this is then granulated, water being added where appropriate.
The granulate is dried overnight at 350, passed through a sieve with a mesh size of 1.2 mm, mixed with the magnesium stearate, and compressed to form biconcave tablets with a diameter of 6 mm.

| 2.10. Injectables | |
|---|---|
| A Oily vehicle (slow release) | |
| an active ingredient | 0.1–1.0 g |
| groundnut oil | ad 100 ml |
| an active ingredient | 0.1–1.0 g |
| sesame oil | ad 100 ml |

The active ingredient is dissolved in part of the oil whilst stirring and, if required, with gentle heating, then after cooling made up to the desired volume and sterile-filtered through a suitable membrane filter with a pore size of 0.22 mm.

| B Water-miscible solvent (average rate of release) | |
|---|---|
| an active ingredient | 0.1–1.0 g |
| 4-hydroxymethyl-1,3-dioxolane (glycerol formal) | 40 g |
| 1,2-propanediol | ad 100 ml |
| an active ingredient | 0.1–1.0 g |
| glycerol dimethyl ketal | 40 g |
| 1,2-propanediol | ad 100 ml |

The active ingredient is dissolved in part of the solvent whilst stirring, filled to the desired volume and sterile-filtered through an appropriate membrane filter with a pore size of 0.22 mm.

| C. Aqueous solubilisate (rapid release) | |
|---|---|
| an active ingredient | 0.1–1.0 g |
| polyethoxylated castor oil (40 ethylene oxide units) | 10 g |
| 1,2-propanediol | 20 g |
| benzyl alcohol | 1 g |
| aqua ad inject. | ad 100 ml |
| an active ingredient | 0.1–1.0 g |
| polyethoxylated sorbitan monooleate (20 ethylene oxide units) | 8 g |
| 4-hydroxymethyl-1,3-dioxolane (glycerol formal) | 20 g |
| benzyl alcohol | 1 g |
| aqua ad inject. | ad 100 ml |

Preparation: The active ingredient is dissolved in the solvents and the surfactant, and made up with water to the desired volume. Sterile filtration through an appropriate membrane filter of 0.22 mm pore size.
The aqueous systems may also preferably be used for oral and/or intraruminal application.

| 2.11. Pour on | |
|---|---|
| A | |
| active ingredient | 10% |
| epoxidised soybean oil | 5% |
| oleyl alcohol | 85% |
| B | |
| active ingredient | 20% |
| pyrrolidin-2-one | 15% |
| isopropyl myristate | 65% |

Further biologically active substances or additives, which are neutral towards the compounds of formula (I) and do not have a harmful effect on the host animal to be treated, as well as mineral salts or vitamins, may be added to the described compositions.

3. BIOLOGICAL EXAMPLES

A. Insecticidal Activity

3.1. Activity Against *Aphis craccivora*

Pea seedlings are infected with *Aphis craccivora*, subsequently sprayed with a spray mixture containing 100 ppm of active ingredient, and then incubated at 20° C. The percentage reduction of the population (% response) is determined 3 and 6 days later by comparing the total number of dead aphids on the treated plants with those on the untreated plants.

The compounds of tables 1 to 4 show good efficacy in this test.

3.2. Activity Against *Diabrotica balteata*

Corn seedlings are sprayed with an aqueous emulsion spray mixture containing 100 ppm of active ingredient, when the spray coating has dried on they are colonised with 10 larvae of the second stage of *Diabrotica balteata* and then placed in a plastic container. The percentage reduction of the population (% response) is determined 6 days later by comparing the total number of dead larvae on the treated plants with those on the untreated plants.

The compounds of tables 1 to 4 show good efficacy in this test; especially the compounds 1.1 and 2.4 show an efficacy of over 80%.

3.3. Activity Against *Heliothis virescens*

Young soya plants are sprayed with an aqueous emulsion spray mixture containing 100 ppm of active ingredient, when the spray coating has dried on they are colonised with 10 caterpillars of the first stage of *Heliothis virescens* and then placed in a plastic container. The percentage reduction of the population and of the feeding damage (% response) is determined 6 days later by comparing the total number of dead caterpillars and the feeding damage on the treated plants with those on the untreated plants.

The compounds of tables 1 to 4 show good efficacy in this test; especially the compound 1.17 shows an efficacy of over 80%.

3.4. Activity Against *Spodoptera littoralis*

Young soya plants are sprayed with an aqueous emulsion spray mixture containing 100 ppm of active ingredient, when the spray coating has dried on they are colonised with 10 caterpillars of the third stage of *Spodoptera littoralis* and then placed in a plastic container. The percentage reduction of the population and of the feeding damage (% response) is determined 3 days later by comparing the total number of dead caterpillars and the feeding damage on the treated plants with those on the untreated plants.

The compounds of tables 1 to 4 show good efficacy in this test; especially the compounds 1.1 to 1.6, 1.8 to 1.14, 1.16, 1.16 to 1.25 and 2.4 show an efficacy of over 80%.

3.5. Activity Against *Nilaparvata lugens*

Rice plants are sprayed with an aqueous emulsion spray mixture containing 400 ppm of active ingredient. After the spray coating has dried on, the rice plants are colonised with plant and leaf-hopper larvae of the second and third stage. 21 days later they are evaluated. The percentage reduction of the population (% response) is determined by comparing the number of surviving plant and leaf-hoppers on the treated plants with those on the untreated plants.

The compounds of tables 1 to 4 show good efficacy in this test.

3.6. Activity Against *Crocidolomia binotalis*

Young cabbage plants are sprayed with an aqueous emulsion spray mixture containing 400 ppm of active ingredient. After the spray coating has dried on, the cabbage plants are colonised with 10 caterpillars of the third stage of *Crocidolomia binotalis* and placed in a plastic container. Three days later they are evaluated. The percentage reduction of the population and of the feeding damage (% response) is determined by comparing the total number of dead caterpillars and the feeding damage on the treated plants with those on the untreated plants.

The compounds of tables 1 to 4 show good efficacy in this test.

3.7. Activity Against *Anthonomus grandis*

Young cotton plants are sprayed with an aqueous emulsion spray mixture containing 400 ppm of active ingredient. After the spray coating has dried on, the cotton plants are colonised with 10 adult *Anthonomus grandis* and placed in a plastic container. Three days later they are evaluated. The percentage reduction of the population and of the feeding damage (% response) is determined by comparing the total number of dead beetles and the feeding damage on the treated plants with those on the untreated plants.

The compounds of tables 1 to 4 show good efficacy in this test.

3.8. Activity Against *Aonidiella aurantii*

Potato tubers are colonised with crawlers of *Aonidiella aurantii*. After about 2 weeks, the potatoes are immersed in an aqueous emulsion or suspension spray mixture containing 400 ppm of active ingredient. After the tubers have dried off, they are incubated in a plastic container. Evaluation is effected 10 to 12 weeks later by comparing the survival rate of the crawlers of the first secondary generation of the treated population with that of untreated control batches.

The compounds of tables 1 to 4 show good efficacy in this test.

3.9. Activity Against *Bemisia tabaci*

Dwarf bean plants are placed into gauze cages and colonised with adults of *Bemisia tabaci*. Following oviposition, all adults are removed. Ten days later, the plants and the nymphs thereon are sprayed with an aqueous emulsion spray mixture containing 400 ppm of the active ingredient. After a further 14 days, the percentage hatching rate of the eggs is compared with that of untreated controls.

The compounds of tables 1 to 4 show good efficacy in this test.

B. Acaricidal Activity

3.10. Activity Against *Tetranychus urticae*

Young bean plants are colonised with a mixed population of *Tetranychus urticae*, sprayed one day later with an aqueous emulsion spray mixture containing 100 ppm of active ingredient, incubated for 6 days at 25° C. and then evaluated. The percentage reduction of the population (% response) is determined by comparing the total number of dead eggs, larvae, and adults on the treated plants with those on the untreated plants.

The compounds of tables 1 to 4 show good efficacy in this test; especially the compounds 1.1 1.5, 1.11 to 1.19 and 1.21 show an efficacy of over 80%.

3.11. Activity Against *Panonychus ulmi* (resistant to organophosphates und carbaryl)

Apple seedlings are colonised with adult females of *Panonychus ulmi*. After seven days, the infected plants are sprayed with an aqueous emulsion spray mixture containing 400 ppm of the test compound until they are dripping wet, and cultivated in the greenhouse. After 14 days, they are evaluated. The percentage reduction of the population (% response) is determined by comparing the number of dead spider mites on the treated plants with those on the untreated plants.

The compounds of tables 1 to 4 show good efficacy in this test.

C. Ectoparasiticidal Activity 3.12. Control of Adult Fleas on Cats by Means of Pour-on Application To determine the efficacy of the test substances against adult fleas, four groups each of two cats are used. Each cat is infected with 100 cat fleas [*Ctenocephalides felis* (Bouché)] and treated with 20 mg of active substance per kg body weight. Treatment is effected by applying the formulation to a specific location on the cat's neck. One group is infected with fleas, but only with a placebo, i.e. a formulation with no active ingredient, and is used as the control. A further group is treated with nitenpyram as the substance for comparison, and the two remaining groups are treated with the test substances. Evaluation is made by combing the surviving fleas from the fur and counting them, then comparing them with the number of fleas from the control group and from the group treated with nitenpyram. In general, each cat is infected directly after treatment on day 0 with 100 fleas. On day +1, each animal is combed and the number of surviving fleas is determined. Afterwards, the surviving fleas are put back on the identical cat and the combing and evaluating are repeated after 24 hours. The fleas still surviving after these 24 hours are not put back on the cat again. On days +3, +7, +9, +14, +21, +28, +35, +42 and +49, the described procedure is repeated, and in this way the efficacy and duration of efficacy are determined. On each of the days on which any surviving fleas are combed out—with the exception of the control group—a blood sample of ca. 2.7 ml is taken from each cat and the content of active substance measured. The efficacy is determined using the following formula:

$$\% \text{ activity} = \frac{\text{number of live fleas/control animal} - \text{number of live fleas/test animal}}{\text{number of live fleas/control animal}} * 100$$

This shows that the substances of formula (I) according to the invention bring about outstanding long-term efficacy compared with nitenpyram.

For dogs, the test is exactly the same. Similar effects are also observed if the substances are applied not as pour-on, but as an injection solution.

3.13. Control of Adult Fleas on Cats by Means of Subcutaneous Injection

To determine the efficacy of the test substances against adult fleas, four groups each of two cats aged between 1.5 and 4 years, are used. Each cat is infected with 100 cat fleas [*Ctenocephalides felis* (Bouché)] and treated with 20 mg of active substance per kg body weight. Treatment is effected by subcutaneous injection of a solution of the active ingredient behind the left shoulder blade. One group is infected with fleas, but treated only with a placebo, i.e. a formulation with no active ingredient, and is used as the control. A further group is treated with nitenpyram as the substance for comparison, and the two remaining groups are treated with the test substances. Evaluation is effected in each case analogously to the above example.

This shows that the substances of tables 1 to 4 according to the invention bring about outstanding long-term efficacy after subcutaneous injection, compared with nitenpyram. A similar test on dogs leads to comparable results.

What we claim is:
1. A compound of formula

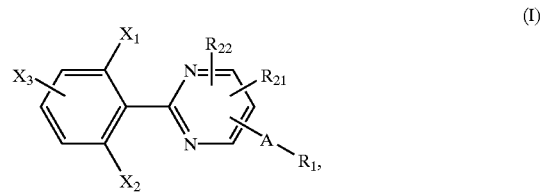

wherein
$R_1$ is unsubstituted or mono- to penta-substituted naphthyl, wherein the substituents are selected from the group consisting of OH, halogen, CN, $C_1$–$C_6$-alkyl, $C_3$–$C_8$-cycloalkyl, $C_1$–$C_6$-alkyl-$C_3$–$C_8$-cycloalkyl, $C_3$–$C_8$-cycloalkyl-$C_1$–$C_6$-alkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$-cycloalkylthio, $C_1$–$C_6$-haloalkylthio, $C_3$–$C_8$-halocycloalkylthio, $C_1$–$C_6$-alkylsulfinyl, $C_3$–$C_8$-cycloalkylsulfinyl, $C_1$–$C_6$-haloalkylsulfinyl, $C_3$–$C_8$-halocycloalkylsulfinyl, $C_1$–$C_6$-alkylsulfonyl, $C_3$–$C_8$-cycloalkylsulfonyl, $C_1$–$C_6$-haloalkylsulfonyl, $C_3$–$C_8$-halocycloalkylsulfonyl, $C_2$–$C_8$-alkenyl, $C_2$–$C_8$-alkinyl, $C_1$–$C_6$-alkylcarbonyl, —C(=NOR$_6$)—$C_1$–$C_6$-alkyl, $R_7$; unsubstituted or mono- to penta-substituted phenyl, wherein the substituents are selected from the group consisting of OH, halogen, CN, NO$_2$, $C_1$–$C_6$-alkyl, $C_3$–$C_8$-cycloalkyl, $C_1$–$C_6$-alkyl-$C_3$–$C_8$-cycloalkyl, $C_3$–$C_8$-cycloalkyl-$C_1$–$C_6$-alkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$-cycloalkylthio, $C_1$–$C_6$-haloalkylthio, $C_3$–$C_8$-halocycloalkylthio, $C_1$–$C_6$-alkylsulfinyl, $C_3$–$C_8$-cyctoalkylsulfinyl, $C_1$–$C_6$-haloalkylsulfinyl, $C_3$–$C_8$-halocycloalkylsulfinyl, $C_1$–$C_6$-alkylsulfonyl, $C_3$–$C_8$-cycloalkylsulfonyl, $C_1$–$C_6$-haloalkylsulfonyl, $C_3$–$C_8$-halocycloalkylsulfonyl, $C_2$–$C_8$-alkenyl, $C_2$–$C_8$-alkinyl, $C_1$$C_6$-alkylcarbonyl, —C(=NOR$_6$)—$C_1$–$C_6$-alkyl and $R_7$; unsubstituted or mono- to penta-substituted phenoxy, unsubstituted or mono- to penta-substituted phenylthio, unsubstituted or mono- to penta-substituted phenylamino and unsubstituted or mono- to penta-substituted —N(phenyl)($C_1$–$C_6$-alkyl), wherein the substituents are selected from the group consisting of halogen, CN, NO$_2$, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-alkylthio, $C_3$–$C_8$-cycloalkylthio, $C_1$–$C_6$-haloalkylthio and $C_3$–$C_8$-halocycloalkylthio;

A is $(CR_{11}R_{12})_p$, $O(CR_{11}R_{12})_p$, $S(O)_n(CR_{11}R_{12})_p$, unsubstituted or substituted $C_2$–$C_8$-alkenylen, unsubstituted or substituted $C_2$–$C_8$-alkinylen, wherein the substituents are selected from the group consisting of $R_{11}$ and $R_{12}$; or $NR_3(CH_2)_p$;

$R_3$ is H, $C_1$–$C_6$-alkyl, $C_3$–$C_8$-cycloalkyl, $C_1$14 $C_6$-haloalkyl, $C_2$–$C_8$-alkenyl, $C_2$–$C_8$-alkinyl, aryl-$C_1$–$C_6$-alkyl, $(CH_2)_pC(O)R_4$ or $C_1$–$C_6$-alkoxy-$C_2$–$C_6$-alkyl;

$R_4$ is H, $C_1$–$C_6$-alkyl, $C_3$–$C_8$-cycloalkyl, $C_1$–$C_6$-haloalkyl, $C_1$–$C_6$-alkoxy, $N(R_5)_2$ or $C_1$–$C_6$-alkoxy-$C_2$–$C_6$-alkyl;

$R_5$ is H, $C_1$–$C_6$-alkyl, $C_3$–$C_8$-cycloalkyl, $C_1$–$C_6$-haloalkyl, or aryl-$C_1$–$C_6$-alkyl;

$R_6$ is H, $C_1$–$C_6$alkyl or $C_3$–$C_8$-cycloalkyl;

$R_7$ is

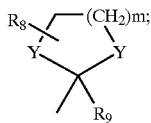

$R_8$ and $R_9$ are independently of one another H or $C_1$–$C_6$-alkyl;

$X_1$ and $X_2$, are independently of one another $R_{10}$;

$X_3$ is H or $R_{10}$;

$R_{10}$ is halogen, CN, $NO_2$, $C_1$–$C_6$-alkyl, $C_3$–$C_8$-cycloalkyl, $C_1$–$C_6$-haloalkyl, $C_3$–$C_8$-halocycloalkyl, $C_1$–$C_6$-alkoxy, $C_3$–$C_8$-cycloalkoxy, $C_1$–$C_6$-haloalkoxy, $C_3$–$C_8$-halocycloalkoxy, $C_1$–$C_6$-alkylthio, $C_3$–$C_8$-cycloalkylthio, $C_1$–$C_6$-haloalkylthio or $C_3$–$C_8$-halocycloalkylthio;

$R_{21}$ and $R_{22}$, are independently of one another H, halogen, CN, $NO_2$, $C_1$–$C_6$-alkyl, $C_3$–$C_8$cycloalkyl, $C_1$–$C_6$-haloalkyl, or $C_3$–$C_8$halocycloalkyl;

m is 1, 2, 3 or 4;

n is 0, 1 or 2;

p is 0, 1, 2, 3, 4, 5, or 6; and

Y is O or S;

as well as the physiologically acceptable addition compounds, and where appropriate the E/Z-isomers, the mixtures of E/Z isomers and/or the tautomers, in each case in the free form or in agrochemically employable salt form.

2. A compound according to claim 1 of formula (I) in the free form.

3. A compound according to claim 1 of formula (I), wherein $X_1$ and $X_2$, independently of one another, are halogen, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio or $C_1$–$C_4$haloalkylthio.

* * * * *